United States Patent
Inoue et al.

(10) Patent No.: US 10,813,617 B2
(45) Date of Patent: Oct. 27, 2020

(54) RADIATION EMITTING DEVICE, METHOD FOR CONTROLLING RADIATION EMITTING DEVICE, AND PROGRAM

(71) Applicant: FUJIFILM Corporation, Tokyo (JP)

(72) Inventors: Tomoki Inoue, Kanagawa (JP); Yasunori Ohta, Kanagawa (JP); Ryosuke Ogura, Kanagawa (JP); Yuzo Aoshima, Kanagawa (JP); Fumito Nariyuki, Kanagawa (JP); Masayoshi Matsuura, Kanagawa (JP); Haruyasu Nakatsugawa, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 224 days.

(21) Appl. No.: 15/846,338

(22) Filed: Dec. 19, 2017

(65) Prior Publication Data

US 2018/0116623 A1 May 3, 2018

Related U.S. Application Data

(63) Continuation of application No. PCT/JP2016/002888, filed on Jun. 15, 2016.

(30) Foreign Application Priority Data

Jun. 22, 2015 (JP) ................. 2015-124512

(51) Int. Cl.
*A61B 6/08* (2006.01)
*G01N 23/04* (2018.01)
(Continued)

(52) U.S. Cl.
CPC ............... *A61B 6/542* (2013.01); *A61B 6/00* (2013.01); *A61B 6/06* (2013.01); *A61B 6/08* (2013.01);
(Continued)

(58) Field of Classification Search
CPC .... A61B 6/00; A61B 6/06; A61B 6/08; A61B 6/40; A61B 6/461; A61B 6/542;
(Continued)

(56) References Cited

U.S. PATENT DOCUMENTS

| | | | |
|---|---|---|---|
| 5,539,798 A | 7/1996 | Asahina et al. | |
| 6,502,984 B2* | 1/2003 | Ogura | A61B 6/06 378/206 |

(Continued)

FOREIGN PATENT DOCUMENTS

| | | | |
|---|---|---|---|
| DE | 10 2012 202 498 A1 | 8/2013 | |
| DE | 102012202498 A1 * | 8/2013 | |

(Continued)

OTHER PUBLICATIONS

"Portable X-ray Equipment IPF-21 Inverter type", Toshiba Medical Supply Co., Ltd., Radiography Apparatus, Searched on Jul. 30, 1999 Internet URL:http://www.toshiba-iryouyouhin.co.jp/tmeds/xrays/ipf21.html (4 pages total).

(Continued)

*Primary Examiner* — Irakli Kiknadze
(74) *Attorney, Agent, or Firm* — Sughrue Mion, PLLC

(57) ABSTRACT

Provided are a radiation emitting device forming a radiography apparatus, a method for controlling the radiation emitting device, and a program which can reduce power consumption. A radiation emitting device includes a radiation source, a collimator that sets a radiation field region, imaging unit for capturing an image of an imaging target, a display unit that displays the image captured by the imaging unit, an exposure switch, and a control unit that issues a collimator driving command to direct the collimator to set the radiation field region determined from the captured image to the collimator in a case in which the exposure switch is operated.

19 Claims, 13 Drawing Sheets

(51) Int. Cl.
  *A61B 6/00*   (2006.01)
  *H05G 1/64*   (2006.01)
  *H05G 1/00*   (2006.01)
  *A61B 6/06*   (2006.01)

(52) U.S. Cl.
  CPC .............. *A61B 6/40* (2013.01); *A61B 6/461* (2013.01); *H05G 1/00* (2013.01); *H05G 1/64* (2013.01)

(58) Field of Classification Search
  CPC ....... A61B 6/4035; A61B 6/465; A61B 6/469; A61B 6/488; A61B 6/505; A61B 6/54; A61B 6/4405; A61B 6/463; A61B 6/547; A61B 6/462; A61B 6/548; A61B 6/0492; A61B 6/4208; A61B 6/587; A61B 6/4266; A61B 6/04; A61B 6/4291; A61B 6/588; A61B 6/4441; A61B 6/025; A61B 6/502; A61B 6/4233; A61B 6/4283; A61B 6/4411; A61B 6/5241; A61B 6/56; A61B 6/467; A61B 6/563; A61B 6/468; A61B 6/508; A61B 2560/0271; A61B 6/48; A61B 6/032; A61B 6/037; A61B 6/0407; A61B 6/4452; H05G 1/00; H05G 1/64; G21K 1/02; G21K 1/10; G01B 11/303; G01B 9/04; G01B 11/25; G01J 9/00; G02B 26/06; H01J 2201/30469; H01J 2235/062; H01J 2235/068; H02H 9/046; G01N 2223/076; G01N 23/223; G01N 21/65; G01N 21/85; G01N 2223/00; H01L 21/822; H01L 23/5223; H01L 23/528; H01L 27/0255; H01L 27/0288; H01L 27/04; H01L 27/1203; G01T 1/1611; G01T 1/1642
  USPC ..................................... 378/62, 63, 205, 206
  See application file for complete search history.

(56) References Cited

U.S. PATENT DOCUMENTS

| | | | | |
|---|---|---|---|---|
| 7,076,027 B2 * | 7/2006 | Matsumoto | ............... | A61B 6/06 348/E5.087 |
| 7,494,276 B2 * | 2/2009 | Borgmann | ............... | A61B 6/08 378/162 |
| 7,916,834 B2 * | 3/2011 | Piorek | .................. | G01N 23/223 378/102 |
| 8,199,876 B2 * | 6/2012 | Graumann | ............... | A61B 6/02 378/63 |
| 8,351,568 B2 * | 1/2013 | Minnigh | ............... | A61B 6/4266 378/204 |
| 8,827,554 B2 * | 9/2014 | Lalena | ..................... | A61B 6/46 378/206 |
| 8,873,708 B2 * | 10/2014 | Sugiyama | ................ | A61B 6/06 378/151 |
| 2008/0002028 A1 * | 1/2008 | Miyata | .................... | H04N 5/225 348/169 |
| 2009/0136000 A1 | 5/2009 | Nishii et al. | | |
| 2009/0232273 A1 | 9/2009 | Sendai | | |
| 2011/0293070 A1 | 12/2011 | Kamiya et al. | | |
| 2013/0272502 A1 | 10/2013 | Watanabe et al. | | |
| 2014/0064447 A1 | 3/2014 | Ogura et al. | | |
| 2014/0241500 A1 * | 8/2014 | Yasuda | ..................... | A61B 6/06 378/62 |
| 2015/0055753 A1 * | 2/2015 | Tajima | ..................... | A61B 6/08 378/62 |
| 2015/0228071 A1 | 8/2015 | Jockel et al. | | |

FOREIGN PATENT DOCUMENTS

| | | |
|---|---|---|
| JP | 55-80900 A | 6/1980 |
| JP | 55-80900 U | 6/1980 |
| JP | 03-29109 U | 3/1991 |
| JP | 06-217973 A | 8/1994 |
| JP | 2007-111120 A | 5/2007 |
| JP | 2009-131323 A | 6/2009 |
| JP | 2009-219654 A | 10/2009 |
| JP | 2011-245062 A | 12/2011 |
| JP | 2012-29889 A | 2/2012 |
| JP | 2013-17630 A | 1/2013 |
| JP | 2013-158431 A | 8/2013 |
| JP | 2013-220218 A | 10/2013 |
| JP | 2014-64774 A | 4/2014 |
| JP | 2014-221136 A | 11/2014 |
| JP | 2014221136 A * | 11/2014 |
| WO | 2014/033614 A1 | 3/2014 |

OTHER PUBLICATIONS

International Search Report for PCT/JP2016/02888, dated Oct. 25, 2016.
Translation of Written Opinion dated Oct. 25, 2016, issued by the International Bureau in counterpart Application No. PCT/JP2016/002888.
International Preliminary Report on Patentability issued from the International Bureau in counterpart International Application No. PCT/JP2016/002888, dated Dec. 26, 2017.
Communication dated Aug. 16, 2018 from the European Patent Office in counterpart application No. 16813929.3.
Communication dated Dec. 11, 2018, from the Japanese Patent Office in counterpart application No. 2017-524619.
Communication dated Jul. 9, 2019, from the Japanese Patent Office in counterpart Application No. 2017-524619.
Communication dated Mar. 27, 2020 from the State Intellectual Property Office of the P.R.C. in Application No. 201680036015.0.

* cited by examiner

RADIATION EMITTING DEVICE, METHOD FOR CONTROLLING RADIATION EMITTING DEVICE, AND PROGRAM

CROSS-REFERENCE TO RELATED APPLICATIONS

This application is a continuation application of International Application No. PCT/JP2016/002888 filed Jun. 15, 2016, the disclosure of which is incorporated herein by reference in its entirety. Further, this application claims priority from Japanese Patent Application No. 2015-124512, filed Jun. 22, 2015, the disclosure of which is incorporated herein by reference in its entirety.

BACKGROUND OF THE INVENTION

1. Field of the Invention

The present invention relates to a radiation emitting device for capturing a radiographic image, a method for controlling the radiation emitting device, and a computer-readable storage medium.

2. Description of the Related Art

For example, as disclosed in JP2012-29889A and Toshiba Medical Supply Co., Ltd., Radiography Apparatus IPF-21, [online], [Searched on Jul. 30, 1999], Internet <URL: http://www.toshiba-iryouyouhin.co.jp/tmeds/xrays/ipf21.html>, a portable radiation emitting device has been proposed which is provided with only a minimum number of components for emitting radiation, such as a radiation source and an electric circuit, and can be operated by an operator while being held in the hand. This type of portable radiation emitting device is light enough to be operated by the operator while being held in the hand and is advantageous in capturing an image of an object in various directions.

In a case in which the portable radiation emitting device is used to capture a radiographic image of a subject, a radiation detector (a so-called "flat panel detector") that records a radiographic image indicating a subject using radiation that has been emitted and transmitted through the subject is generally used. As the radiation detector, a cassette-type radiation detector has been known in which, for example, an image detection unit, a battery for driving, and a control unit, such as an electric circuit related to driving, are accommodated in a housing. The radiation detector is located so as to face the radiation emitting device, with a subject interposed therebetween. In this state, the radiation emitting device is driven. Then, radiation transmitted through the subject is emitted to the radiation detector and a radiographic image indicated by the radiation transmitted through the subject is acquired.

In a radiography apparatus in which the radiation emitting device and the radiation detector are separately provided, in order to appropriately set a radiation field, a method has been proposed which captures an image of a subject with a camera to acquire an optical image indicating the surface of the subject and matches the radiation field with the range indicated by the optical image (see JP1994-217973A (JP-H06-217973A)).

However, in the method disclosed in JP1994-217973A (JP-H06-217973A), a collimator that narrows the radiation field is sequentially driven according to the range of the optical image in order to match the radiation field with the range indicated by the acquired optical image, which causes an increase in power consumption.

In particular, the portable radiation emitting device disclosed in Toshiba Medical Supply Co., Ltd., Radiography Apparatus IPF-21, [online], [Searched on Jul. 30, 1999], Internet <URL: http://www.toshiba-iryouyouhin.co.jp/tmeds/xrays/ipf21.html> is generally configured such that it is driven by a battery in order to reduce the size and weight of the device. Therefore, in a case in which power consumption increases, the life of the battery is reduced, which causes a reduction in operating rate.

SUMMARY OF THE INVENTION

The invention has been made in view of the above-mentioned problems and an object of the invention is to provide a radiation emitting device, a method for controlling the radiation emitting device, and a program that reduce power consumption.

A first radiation emitting device according to the invention comprises: a radiation source that emits radiation to an imaging target; a collimator that sets a radiation field region; imaging unit for capturing an image of the imaging target; a display unit that displays the image captured by the imaging unit; an exposure switch that drives the radiation source; and a control unit that issues a collimator driving command to direct the collimator to set the radiation field region determined from the captured image displayed by the display unit to the collimator in a case in which the exposure switch is operated.

A second radiation emitting device according to the invention comprises: a radiation source that emits radiation to an imaging target; a collimator that sets a radiation field region; a visible light source that emits visible light; a stop that matches an irradiation range of the visible light on the imaging target with the radiation field region; imaging unit for capturing an image of the imaging target; a display unit that displays the image captured by the imaging unit; a light irradiation switch that drives the visible light source; and a control unit that issues a collimator driving command to direct the collimator to set the radiation field region determined from the captured image displayed by the display unit to the collimator in a case in which the light irradiation switch is operated.

A first method for controlling a radiation emitting device according to the invention corresponds to the first radiation emitting device. The first method is for controlling a radiation emitting device comprising a radiation source that emits radiation to an imaging target, a collimator that sets a radiation field region, imaging unit for capturing an image of the imaging target, a display unit that displays the image captured by the imaging unit, and an exposure switch that drives the radiation source and comprises issuing a collimator driving command to direct the collimator to set the radiation field region determined from the captured image displayed by the display unit to the collimator in a case in which the exposure switch is operated.

A second method for controlling a radiation emitting device according to the invention corresponds to the second radiation emitting device. The second method is for controlling a radiation emitting device comprising a radiation source that emits radiation to an imaging target, a collimator that sets a radiation field region, a visible light source that emits visible light, a stop that matches an irradiation range of the visible light on the imaging target with the radiation field region, imaging unit for capturing an image of the imaging target, a display unit that displays the image captured by the imaging unit, and a light irradiation switch that drives the visible light source and comprises issuing a collimator driving command to direct the collimator to set the radiation field region determined from the captured image displayed by the display unit to the collimator in a case in which the light irradiation switch is operated.

In addition, a program that causes a computer to perform the first or second method for controlling a radiation emitting device according to the invention may be provided.

DESCRIPTION OF THE PREFERRED EMBODIMENTS

Figure 1:
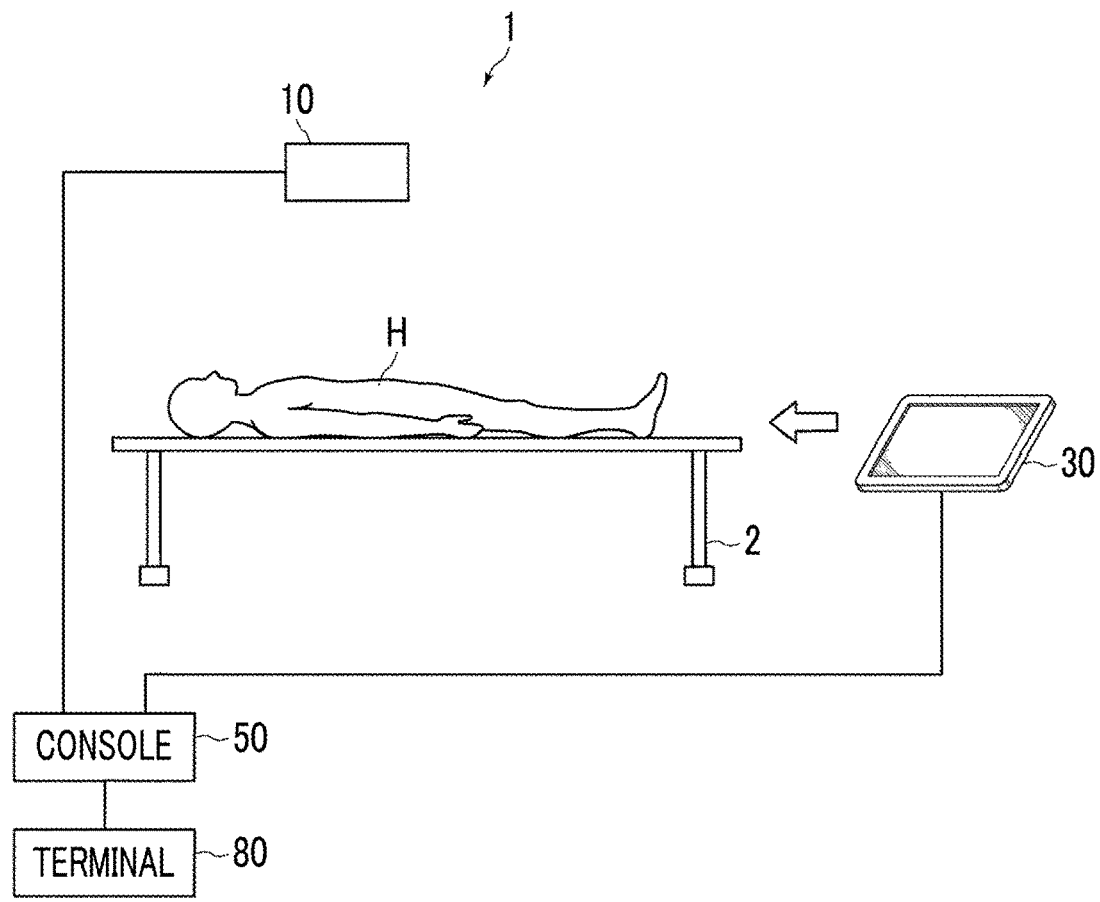
FIG. 1 is a diagram schematically illustrating a radiography apparatus using a radiation emitting device according to an embodiment of the invention.

Hereinafter, embodiments of the invention will be described with reference to the drawings. FIG. 1 is a diagram schematically illustrating a radiography apparatus according to an embodiment of the invention. As illustrated in FIG. 1, a radiography apparatus 1 according to this embodiment includes a portable radiation emitting device 10, a radiation detector 30, and a console 50. For example, in order to acquire a radiographic image of a subject H that lies on a bed 2, the radiation detector 30 is inserted between the subject H and the bed 2, the subject H is irradiated with radiation emitted from the portable radiation emitting device 10, and a radiographic image of the subject H is acquired by the radiation detector 30. In addition, the console 50 is connected to a terminal 80 of, for example, a doctor through a network.

Figure 2:
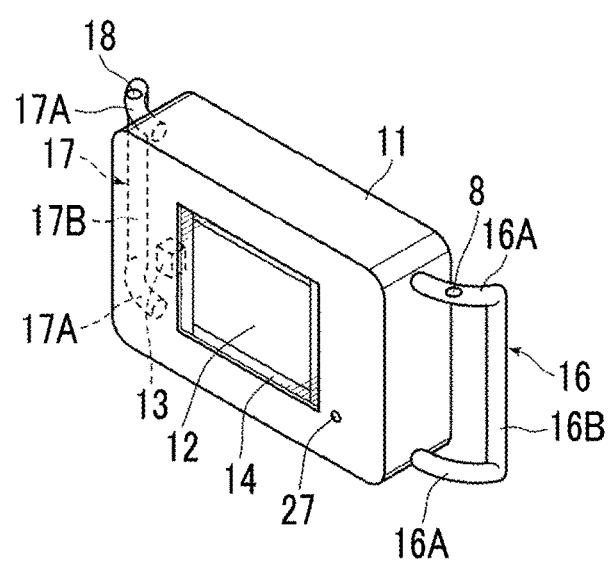
FIG. 2 is a front perspective view illustrating the radiation emitting device.
Figure 3:
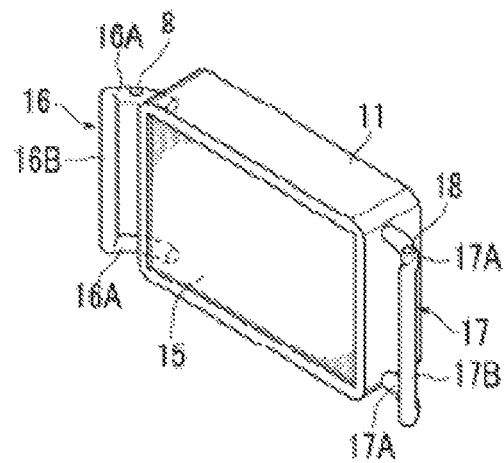
FIG. 3 is a rear perspective view illustrating the radiation emitting device.
Figure 4:
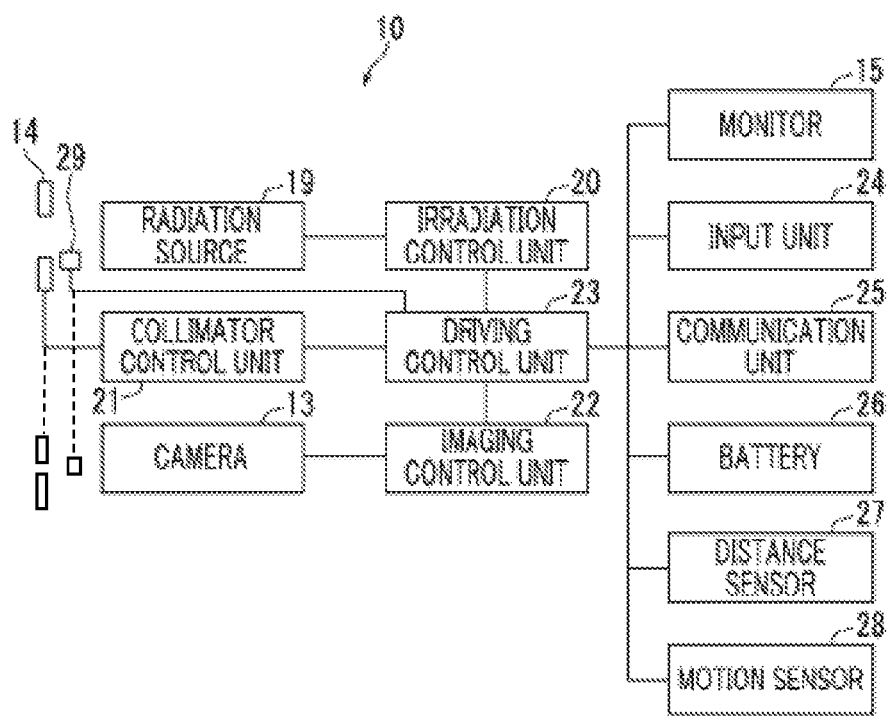
FIG. 4 is a block diagram schematically illustrating the internal configuration of the radiation emitting device.

FIG. 2 is a front perspective view illustrating the radiation emitting device 10. FIG. 3 is a rear perspective view illustrating the radiation emitting device 10. FIG. 4 is a block diagram schematically illustrating the internal configuration of the radiation emitting device 10. As illustrated in the drawings, in the radiation emitting device 10, an emission window 12 through which radiation is emitted, a camera 13 that captures an optical image (captured image) of the surface of the subject H, and a distance sensor 27 are provided on a front surface of a housing 11 with a rectangular parallelepiped shape. A collimator 14 for narrowing the emission range of radiation is seen from the emission window 12. A monitor 15 as a display unit, which is, for example, a liquid crystal display unit, is provided on a rear surface of the housing 11. For example, an optical image acquired by capturing the image of the surface of the subject H using the camera 13, a radiographic image of the subject H, and various kinds of information for setting the radiation emitting device 10 are displayed on the monitor 15. The distance sensor 27 measures the distance between the device 10 and a target object, using a sensor or ultrasonic waves. In addition, the camera 13 is imaging unit according to the invention. In this embodiment, a camera with a zoom function is applied.

Holding portions 16 and 17 are attached to both side surfaces of the housing 11. The holding portion 16 includes two protruding portions 16A that protrude from the upper and lower portions of the side surface of the housing 11 to the side and a connection portion 16B that connects the two protruding portions 16A. The holding portion 17 includes two protruding portions 17A that protrude from the upper and lower portions of the side surface of the housing 11 to the side and a connection portion 17B that connects the two protruding portions 17A. The protruding portions 16A and 17A are curved from a protruding position to the rear surface of the housing 11. The protruding portions 16A and 17A may be inclined from the protruding position to the rear surface of the housing 11, instead of being curved. An operator can hold the holding portions 16 and 17 and move the radiation emitting device 10 to a position where an image of the subject H can be captured. In addition, an imaging button 18 for emitting radiation to capture an image of the subject H is provided in the upper protruding portion 17A of the holding portion 17 that is held by the right hand in a case in which the operator performs an imaging operation. Furthermore, a zoom button 8 for changing the zoom magnification of the camera 13 is provided in the upper protruding portion 16A of the holding portion 16 that is held by the left hand in a case in which the operator performs an imaging operation.

As illustrated in FIG. 4, the housing 11 includes the monitor 15, a radiation source 19, an irradiation control unit 20, a collimator control unit 21, an imaging control unit 22, a driving control unit 23, an input unit 24, a communication unit 25, a battery 26, a distance sensor 27, a motion sensor 28, and a radiation field lamp 29. The irradiation control unit 20, the collimator control unit 21, the imaging control unit 22, the driving control unit 23, and the communication unit 25 are implemented by a program (software) that is operated in a computer, dedicated hardware, or a combination thereof. The program is recorded on a recording medium, such as a digital versatile disc (DVD) or a compact disk read only memory (CD-ROM), and is then distributed. The program is installed in the radiation emitting device 10 from the recording medium. Alternatively, the program is stored in a storage device of a server computer that is connected to a network or a network storage such that it can be accessed from the outside. The program is downloaded and installed in the radiation emitting device 10, if necessary.

The radiation source 19 includes, for example, an X-ray tube, a booster circuit, and cooling means for cooling the X-ray tube.

The irradiation control unit 20 drives the radiation source 19 and controls the amount of radiation emitted to the subject H such that radiation with intensity corresponding to predetermined imaging conditions is emitted to the subject H for only a set period of time. The imaging conditions include a tube voltage (kV value) and an mAs value (a tube current×an irradiation time) corresponding to the body thickness of the subject H. The body thickness of the subject H can be calculated by measuring a source image receptor distance (SID) which is the distance between the device 10 and the surface of the radiation detector 30 and a source object distance (SOD) which is the distance between the device 10 and the surface of the subject H, using the distance sensor 27, and subtracting the SOD from the SID. In addition, the operator may measure the body thickness and input information for setting the imaging conditions including the measured body thickness to the device 10 through the input unit 24. In this embodiment, the information for setting the imaging conditions including, for example, the body thickness is transmitted to the console 50 and the imaging conditions are set in the console 50. The set imaging conditions are transmitted to the radiation emitting device 10. The irradiation control unit 20 controls the emission of radiation to the subject H, using the imaging conditions transmitted from the console 50.

The collimator control unit 21 includes, for example, a driving mechanism, such as a motor for driving the collimator 14 to change the field of the radiation emitted from the radiation source 19 to the subject H, and an electric circuit for controlling the driving mechanism. The collimator control unit 21 controls the driving of the collimator 14 in response to a command from the driving control unit 23. The collimator control unit 21 and the driving control unit 23 correspond to a control unit according to the invention.

The imaging control unit 22 drives the camera 13 to capture an image of the surface of the subject H and acquires an optical image. The driving of the camera 13 includes driving a zoom lens to change a zoom magnification in response to a command from the zoom button 8. Hereinafter, the optical image is referred to as a "captured image G1". In addition, the imaging control unit 22 may perform image processing for improving the quality of the captured image G1 acquired by the camera 13. The captured image G1 acquired by the camera 13 is a motion picture with a predetermined frame rate of, for example, 30 fps.

The driving control unit 23 controls the overall driving operation of the radiation emitting device 10. That is, the driving control unit 23 performs, for example, a process of instructing the irradiation control unit 20 to drive the radiation source 19, a process of instructing the collimator control unit 21 to drive the collimator 14, a process of instructing the imaging control unit 22 to drive the camera 13 such that the captured image G1 is acquired, a process of displaying various kinds of information including the captured image G1 on the monitor 15, a process of instructing the communication unit 25 to exchange various kinds of information with the console 50, a process of monitoring the state of the battery 26, a process of receiving a command from the input unit 24, a process of measuring the distance between the radiation emitting device 10 and an object using the distance sensor 27, a process of detecting the movement of the radiation emitting device 10 using the motion sensor 28, and a process of setting the driving state of the radiation emitting device 10. In addition, each of the above-mentioned processes is performed by the commands from the input unit 24 or the commands that have been transmitted from the console 50 and received by the communication unit 25.

The input unit 24 is a touch-panel-type input unit that is integrated with the monitor 15, receives a command from the operator, and outputs information indicating the command to the driving control unit 23. It is assumed that the imaging button 18 is also included in the input unit 24.

The communication unit 25 performs wireless communication with the console 50 to exchange information. Examples of the information transmitted from the communication unit 25 to the console 50 include the captured image G1, the SID and the SOD measured by the distance sensor 27, the information of the radiation field defined by the collimator 14, movement information detected by the motion sensor 28 which will be described below, and information for setting the imaging conditions set by the operator through the input unit 24. Examples of the information transmitted from the console 50 to the communication unit 25 include a command to change the driving state of the radiation emitting device 10 and information such as imaging conditions. In addition, the radiation emitting device 10 may be connected to the console 50 by a cable, instead of wireless communication, and exchange information with the console 50 in a wired manner. In the latter case, the communication unit 25 has a connector to which the cable is connected.

The motion sensor 28 is a 9-axis motion sensor that detects 3-axis acceleration, 3-axis angular velocity, and 3-axis tilt. The acceleration, angular velocity, and tilt detected by the motion sensor 28 are output as movement information to the driving control unit 23, are used to control the radiation emitting device 10 during imaging, and are transmitted from the communication unit 25 to the console 50. Here, the term "tilt" means a tilt with respect to the position where the radiation emitting device 10 is kept horizontal in a state in which a radiation emission axis, which is an axis aligned with the emission direction of radiation, is aligned with the direction of gravity.

The radiation field lamp 29 is a light emitting element such as a light bulb or a light emitting diode (LED) that emits visible light. The driving control unit 23 controls the turn-on and turn-off of the radiation field lamp 29. When the radiation field lamp 29 is turned on, visible light is emitted to the radiation field in which radiation is emitted on the subject H. The detailed arrangement state of the radiation field lamp 29 will be described in detail below. The radiation field lamp 29 corresponds to a visible light source.

Figure 5:
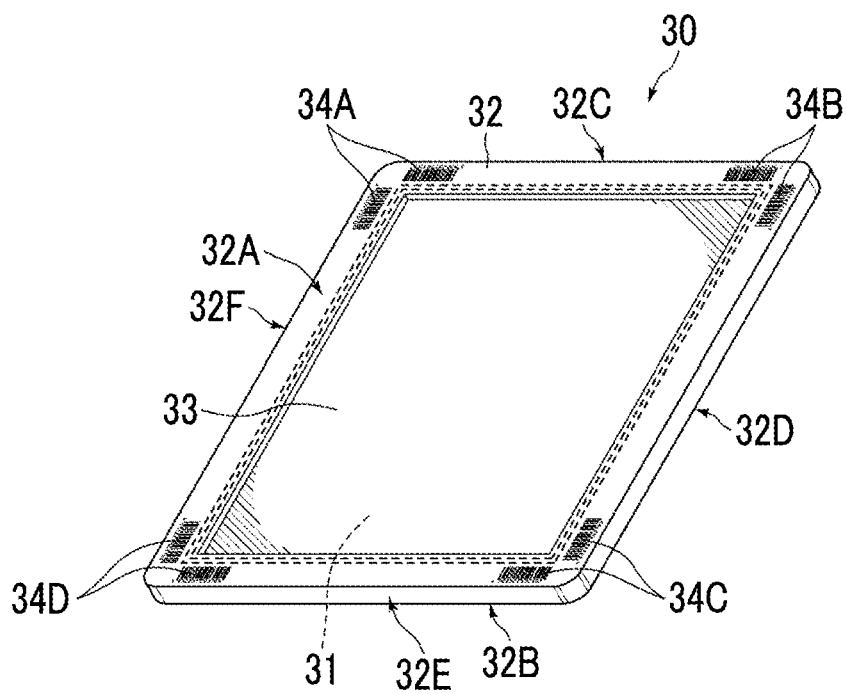
FIG. 5 is a perspective view illustrating the outward appearance of a radiation detector as viewed from a front surface which is a radiation emitting side.
Figure 6:
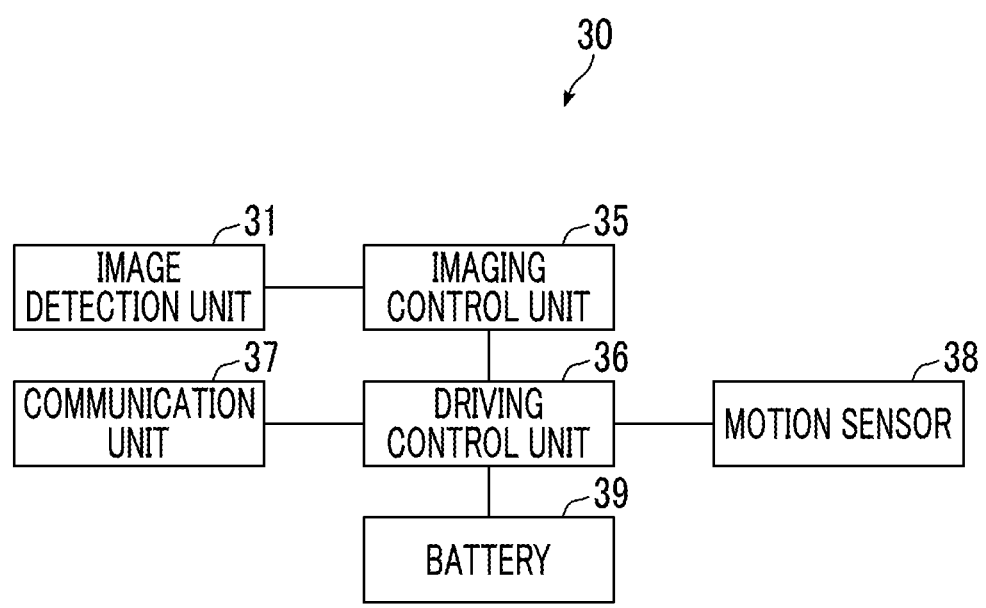
FIG. 6 is a block diagram schematically illustrating the internal configuration of the radiation detector.

Next, the configuration of the radiation detector 30 will be described below. FIG. 5 is a perspective view illustrating the outward appearance of the radiation detector as viewed from the front side which is a radiation emitting side and FIG. 6 is a block diagram schematically illustrating the internal configuration of the radiation detector.

As illustrated in FIG. 5, the radiation detector 30 is a cassette-type radiation detector including a housing 32 that accommodates an image detection unit 31. The image detection unit 31 includes a scintillator (phosphor) that converts incident radiation into visible light and a thin film transistor (TFT) active matrix substrate, as known in the art. A rectangular imaging region in which a plurality of pixels that accumulate charge corresponding to the visible light from the scintillator are arranged is formed on the TFT active matrix substrate. The housing 32 includes, for example, an imaging control unit 35 including a gate driver that applies a gate pulse to a gate of a TFT to switch the TFT and a signal processing circuit that converts the charge accumulated in the pixel into an analog electric signal indicating an X-ray image and outputs the analog electric signal, in addition to the image detection unit 31.

The housing 32 has a rectangular parallelepiped shape having a front surface 32A on which radiation is incident, a rear surface 32B opposite to the front surface 32A, and four side surfaces 32C, 32D, 32E, and 32F. The housing 32 is made of, for example, a conductive resin, and also functions as an electromagnetic shield that prevents the penetration of electromagnetic noise into the radiation detector 30 and the emission of electromagnetic noise from the inside of the radiation detector 30 to the outside. The housing 32 has a size that is based on International Organization for Standardization (ISO) 4090:2001 and is substantially equal to the size of, for example, a film cassette, an imaging plate (IP) cassette, or a computed radiography (CR) cassette.

A transmission plate 33 that transmits radiation is attached to the front surface 32A of the housing 32. The transmission plate 33 has a size that is substantially equal to the size of a radiation detection region of the radiation detector 30 and is made of a carbon material that has a small weight, high rigidity, and high transmittance.

Markers 34A to 34D that indicate identification information for identifying the radiation detector 30 are attached to four corners of the front surface 32A of the housing 32. In this embodiment, each of the markers 34A to 34D includes two bar codes and is attached to the front surface 30A of the radiation detector 30 such that four corners of the detection region of the radiation detector 30 are defined by the two bar codes. A tape with a color unique to the radiation detector 30 may be used as the marker as long as it can identify the radiation detector 30. Here, each of the markers 34A to 34D is a pair of two bar codes. However, in this embodiment, information indicating the vertical direction of the image detection unit 31 provided in the radiation detector 30 is inserted into one of the two bar codes. In this embodiment, the side on which the markers 34A are 34B are attached is an upper side, that is, a top side. In addition, a light emitting element, such as an LED that emits light with a color unique to a cassette, may be used as the marker.

As illustrated in FIG. 6, the housing 32 includes an image detection unit 31, the imaging control unit 35, a driving control unit 36, a communication unit 37, a motion sensor 38, and a battery 39. The imaging control unit 35, the driving control unit 36, and the communication unit 37 are implemented by a program (software) that is operated in a computer, dedicated hardware, or a combination thereof. The program is installed in the radiation detector 30 as in the radiation emitting device 10.

As described above, the imaging control unit 35 includes, for example, the gate driver and the signal processing circuit, controls the driving of the gate driver and the signal processing circuit such that an analog image signal indicating a radiographic image G2 is generated and outputs the analog image signal to the driving control unit 36.

The driving control unit 36 controls the overall driving operation of the radiation detector 30. That is, the driving control unit 36 performs, for example, a process of instructing the imaging control unit 35 to generate an image signal indicating the radiographic image G2, a process of instructing the communication unit 37 to exchange the image signal indicating the radiographic image G2 and various kinds of information with the console 50, a process of detecting the movement of the radiation detector 30 using the motion sensor 38, a process of monitoring the state of the battery 39, and a process of setting the driving state of the radiation detector 30.

The communication unit 37 performs wireless communication with the console 50 to exchange information. Examples of the information transmitted from the communication unit 37 to the console 50 include the image signal indicating the radiographic image G2, movement information detected by the motion sensor 38 which will be described below, information indicating the current driving state of the radiation detector 30, and information indicating the remaining level of the battery 39. An example of the information transmitted from the console 50 to the communication unit 37 is information, such as a command to change the driving state of the radiation detector 30. In addition, the radiation detector 30 may be connected to the console 50 by a cable, instead of wireless communication, and exchange information with the console 50 in a wired manner. In the latter case, the communication unit 37 has a connector to which the cable is connected.

The motion sensor 38 is a 9-axis motion sensor that detects 3-axis acceleration, 3-axis angular velocity, and 3-axis tilt. The acceleration, angular velocity, and tilt detected by the motion sensor 38 are output as movement information to the driving control unit 36 and are transmitted from the communication unit 37 to the console 50. Here, the term "tilt" means a tilt with respect to the position where the radiation detector 30 is kept horizontal.

Figure 7:
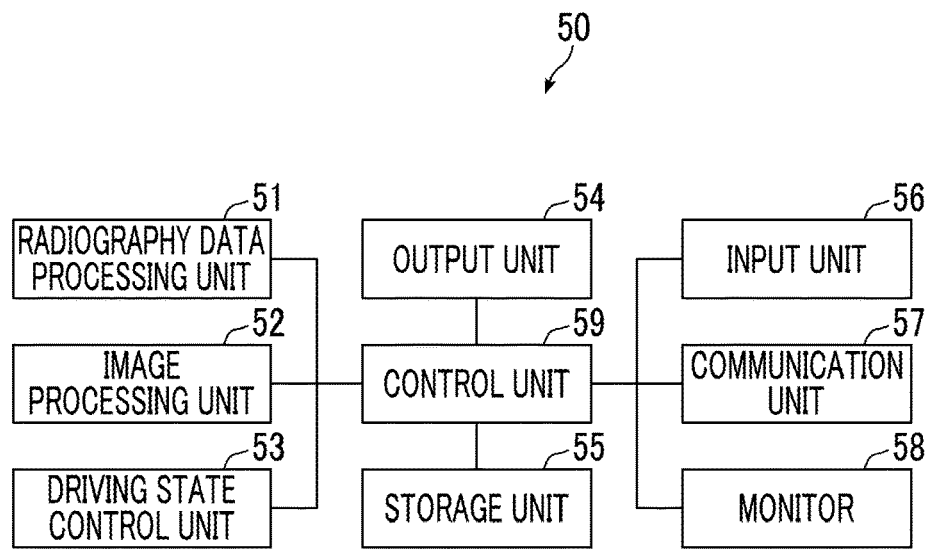
FIG. 7 is a block diagram schematically illustrating the internal configuration of a console.

FIG. 7 is a block diagram schematically illustrating the internal configuration of the console. As illustrated in FIG. 7, the console 50 includes a radiography data processing unit 51, an image processing unit 52, a driving state control unit 53, an output unit 54, a storage unit 55, an input unit 56, a communication unit 57, a monitor 58, and a control unit 59. The radiography data processing unit 51, the image processing unit 52, the driving state control unit 53, the communication unit 57, and the control unit 59 are implemented by a program (software) that is operated in a computer, dedicated hardware, or a combination thereof. The program is installed in the console 50 as in the radiation emitting device 10.

The radiography data processing unit 51 performs data processing, such as A/D conversion, for the image signal indicating the radiographic image G2 of the subject H which has been input from the radiation detector 30. The radiography data processing unit 51 outputs radiographic image data indicating the digital radiographic image G2 subjected to the data processing.

The image processing unit 52 performs predetermined image processing for the radiographic image data output from the radiography data processing unit 51, using image processing parameters stored in the storage unit 55. Examples of the image processing performed by the image processing unit 52 include various types of image processing, such as image calibration (the correction of radiographic image data by calibration data) including pixel defect correction, a process of creating a defect map for performing the pixel defect correction, offset correction, gain correction using a predetermined uniformly exposed image, and shading correction, a gradation correction process, a density correction process, a process of removing scattered rays caused by radiation transmitted through the subject H, and data conversion for converting image data into data for monitor display or data for printout. The image processing unit 52 outputs radiographic image data subjected to the image processing.

In the related art, in a case in which a radiographic image of a subject is captured, a scattered ray removal grid (hereinafter, simply referred to as a grid) is provided between the subject and a radiation detector and imaging is performed, in order to solve the problem that the contrast of the radiographic image is reduced by the scattering of radiation in the subject. In a case in which imaging is performed using the grid, radiation scattered by the subject is less likely to be emitted to the radiation detector, which makes it possible to improve the contrast of the radiographic image. However, for example, the grid is formed by alternately arranging lead that does not transmit radiation and an interspace material, such as aluminum or fiber that is likely to transmit radiation, at a small grating density of about 4.0 lines/mm and is heavy. Therefore, during imaging in, for example, a hospital, it is necessary to put the heavy grid between the patient who lies on the bed and the radiation detector. As a result, a burden on the placement operation and a burden on the patient during imaging increase. In addition, in the case of a convergence-type grid, there is a concern that density unevenness will occur in a radiographic image due to the oblique incidence of radiation. Furthermore, there is a concern that both the image of the subject and moire which is a fine stripe pattern corresponding to the pitch between the grids will be recorded on the radiographic image and the radiographic image will be difficult to see.

For this reason, a method has been performed which captures a radiographic image, without using a grid, and gives the same effect of improving image quality as that obtained by removing scattered rays using a grid to the radiographic image using image processing (for example, U.S. Pat. No. 8,064,676B and "C Fivez et al., Multiresolution contrast amplification in digital radiography with compensation for scattered radiation, 1996 IEEE, pp. 339-342."). This method performs frequency decomposition to decompose a radiographic image into a plurality of frequency components, performs a scattering component removal process of removing contrast or latitude for a low-frequency component which is regarded as a component of a scattered ray, and combines the processed frequency components to acquire a radiographic image from which the components of the scattered rays have been removed. The use of the method for removing the scattered rays using image processing makes it unnecessary to use a grid during imaging. Therefore, it is possible to reduce the burden on the patient during imaging and to prevent density unevenness and the degradation of image quality due to moire.

In the process of removing scattered rays from the radiographic image G2, the body thickness of the subject H and imaging conditions are used. Therefore, in this embodiment, the image processing unit 52 of the console 50 performs the scattered ray removal process, using the body thickness of the subject H measured by the radiation emitting device 10 and the imaging conditions calculated by the control unit 59 which will be described below.

The driving state control unit 53 determines whether the captured image G1 output from the radiation emitting device 10 includes the radiation detector 30 and controls the driving state of at least one of the radiation emitting device 10 or the radiation detector 30 on the basis of whether the captured image G1 includes the radiation detector 30. In this embodiment, it is assumed that the driving state control unit 53 controls the driving state of both the radiation emitting device 10 and the radiation detector 30.

Figure 8:
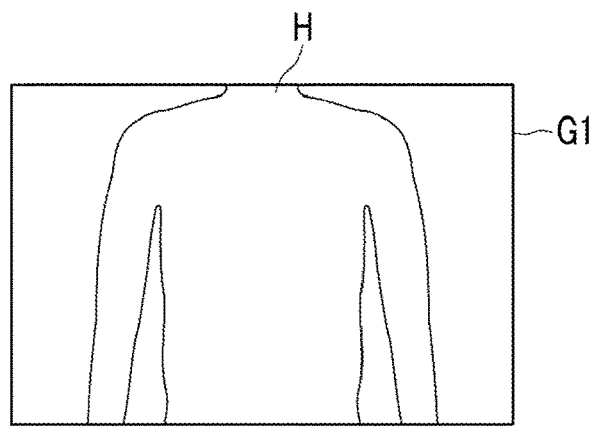
FIG. 8 is a diagram illustrating a captured image including only a subject.
Figure 9:
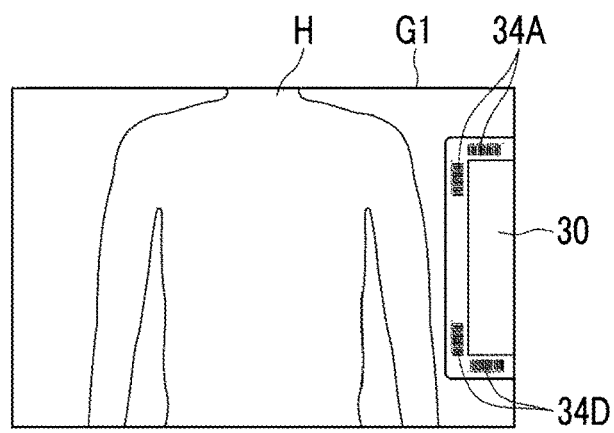
FIG. 9 is a diagram illustrating a captured image including a portion of the radiation detector in addition to the subject.

Next, the detection of the radiation detector 30 in the captured image G1 will be described. In a case in which a radiographic image of the subject H is acquired, the operator places the radiation emitting device 10 to face the subject H and takes the image of the subject H using the camera 13. In this embodiment, it is assumed that the image of the chest of the subject H is captured. Therefore, before imaging, the captured image G1 includes the chest of the subject H as illustrated in FIG. 8. Then, in a case in which an operation of inserting the radiation detector 30 between the bed 2 and the subject H is performed in order to acquire the radiographic image G2 of the subject H, the captured image G1 includes a portion of the radiation detector 30 as illustrated in FIG. 9. Here, the markers 34A to 34D are attached to four corners of the radiation detector 30. The driving state control unit 53 detects whether the captured image G1 includes any one of the markers 34A to 34D. In a case in which the captured image G1 includes any one of the markers 34A to 34D, the driving state control unit 53 determines whether the captured image G1 includes the radiation detector 30.

The control unit 59 transmits radiation detector position information indicating the position of the radiation detector 30 in the captured image G1 from the communication unit 57 to the radiation emitting device 10. The radiation detector position information is a coordinate position indicating the position of the corners of the detection region of the radiation detector 30 on the captured image G1. In this embodiment, the size of the detection region of the radiation detector 30 is stored in the storage unit 55 in advance. The control unit 59 calculates the radiation detector position information from the position of any one of the markers 34A to 34D which has been detected from the captured image G1 by the driving state control unit 53 and the size of the detection region. In addition, in a case in which the radiation detector position information has been known, it is possible to calculate the information of the position of the center of the radiation detector 30 from the size of the detection region of the radiation detector 30. Therefore, the control unit 59 also transmits center position information indicating the position of the center of the radiation detector 30 to the radiation emitting device 10.

Here, the driving state of the radiation emitting device 10 includes a power-off state, a sleep state, a standby state, and a ready state. The power-off state is a state in which power is not supplied from the battery 26 to all of the components of the radiation emitting device 10. The sleep state is a state in which power is supplied to the driving control unit 23, the camera 13, the monitor 15, the imaging control unit 22, and the communication unit 25, the captured image G1 can be acquired, the captured image G1 can be displayed on the monitor 15, information for setting imaging conditions can be received from the input unit 24, and the communication unit 25 can exchange information with the console 50. The standby state is a state in which power is supplied to the irradiation control unit 20 and the collimator control unit 21, imaging conditions can be set, and the collimator 14 can be driven, in addition to the sleep state. The ready state is a state in which power is supplied to the radiation source 19 and the imaging button 18 can be operated to immediately emit radiation from the radiation source 19, in addition to the standby state. Therefore, the power-off state has the lowest power consumption, followed by the sleep state, the standby state, and the ready state.

The driving state of the radiation detector 30 includes a power-off state, a sleep state, and a standby state. The power-off state is a state in which power is not supplied from the battery 39 to all of the components of the radiation detector 30. The sleep state is a state in which power is supplied to the driving control unit 36, the communication unit 37, and the motion sensor 38, the communication unit 37 can exchange information with the console 50, and the motion sensor 38 can detect the movement of the radiation detector 30 and transmit movement information to the console 50. The standby state is a state in which power is supplied to the image detection unit 31 and the imaging control unit 35, in addition to the driving control unit 36 and the communication unit 37, radiation transmitted through the subject H can be detected, and a radiographic image indicating the subject H can be acquired. Therefore, the power-off state has the lowest power consumption, followed by the sleep state and the standby state.

The radiation detector 30 is turned on by the operator in a case in which it starts to be used on each day of use and is in the sleep state before imaging starts. The radiation emitting device 10 is turned on before a pre-imaging operation, which will be described below, starts and is in the sleep state.

In a case in which the radiation detector 30 is detected from the captured image G1, the driving state control unit 53 changes the driving state of the radiation emitting device 10 and the radiation detector 30 to the standby state. In addition, in a case in which the radiation field is set in the radiation emitting device 10 which will be described below, the driving state control unit 53 changes the driving state of the radiation emitting device 10 to the ready state. Therefore, the driving state control unit 53 outputs a command to change the driving state to the control unit 59. In a case in which the command is input, the control unit 59 transmits the command from the communication unit 57 to the radiation emitting device 10 and the radiation detector 30. In a case in which the command is received, the radiation emitting device 10 and the radiation detector 30 change the driving state in response to the command.

The output unit 54 outputs the radiographic image data subjected to the image processing which has been input from the image processing unit 52. The output unit 54 is, for example, a printer that prints out a radiographic image or a storage device that stores radiographic image data.

The storage unit 55 stores, for example, the size of the detection region of the radiation detector 30, image processing parameters for image processing performed by the image processing unit 52, and parameters corresponding to the type of the radiation detector 30 and the body thickness of the subject H for setting the imaging conditions. In addition, the storage unit 55 stores, for example, the radiographic image G2 output from the image processing unit 52 and the captured image G1 transmitted from the radiation emitting device 10. The storage unit 55 may be a semiconductor memory or a recording medium such as a hard disk. In addition, the storage unit 55 may be provided in the console 50. Alternatively, the storage unit 55 may be provided outside the console 50, may be connected to the console 50, and may be used.

The input unit 56 is, for example, a keyboard for inputting various kinds of information to the console 50. In addition, the input unit 56 may be a touch panel.

The communication unit 57 performs wireless communication with the radiation emitting device 10 and the radiation detector 30 to exchange information. In addition, the console 50 may be connected to the radiation emitting device 10 and the radiation detector 30 by a cable, instead of wireless communication, and exchange information with the radiation emitting device 10 and the radiation detector 30 in a wired manner. In the latter case, the communication unit 57 has a connector to which the cable is connected.

The monitor 58 is, for example, a liquid crystal panel and displays the captured image G1 and the radiographic image G2 transmitted from the radiation detector 30.

The control unit 59 controls the overall driving operation of the console 50. That is, the control unit 59 performs, for example, a process of instructing the radiography data processing unit 51 to acquire the radiographic image G2, a process of instructing the image processing unit 52 to perform image processing for the radiographic image G2, a process of instructing the driving state control unit 53 to control the driving state of the radiation emitting device 10 and the radiation detector 30, a process of acquiring the identification information of the radiation detector 30 from any one of the markers 34A to 34D detected by the driving state control unit 53, a process of outputting the radiographic image G2 to the output unit 54, a process of instructing the communication unit 57 to exchange various kinds of information with the radiation emitting device 10 and the radiation detector 30, a process of receiving commands from the input unit 56, and a process of displaying various kinds of information on the monitor 58.

Figure 10:
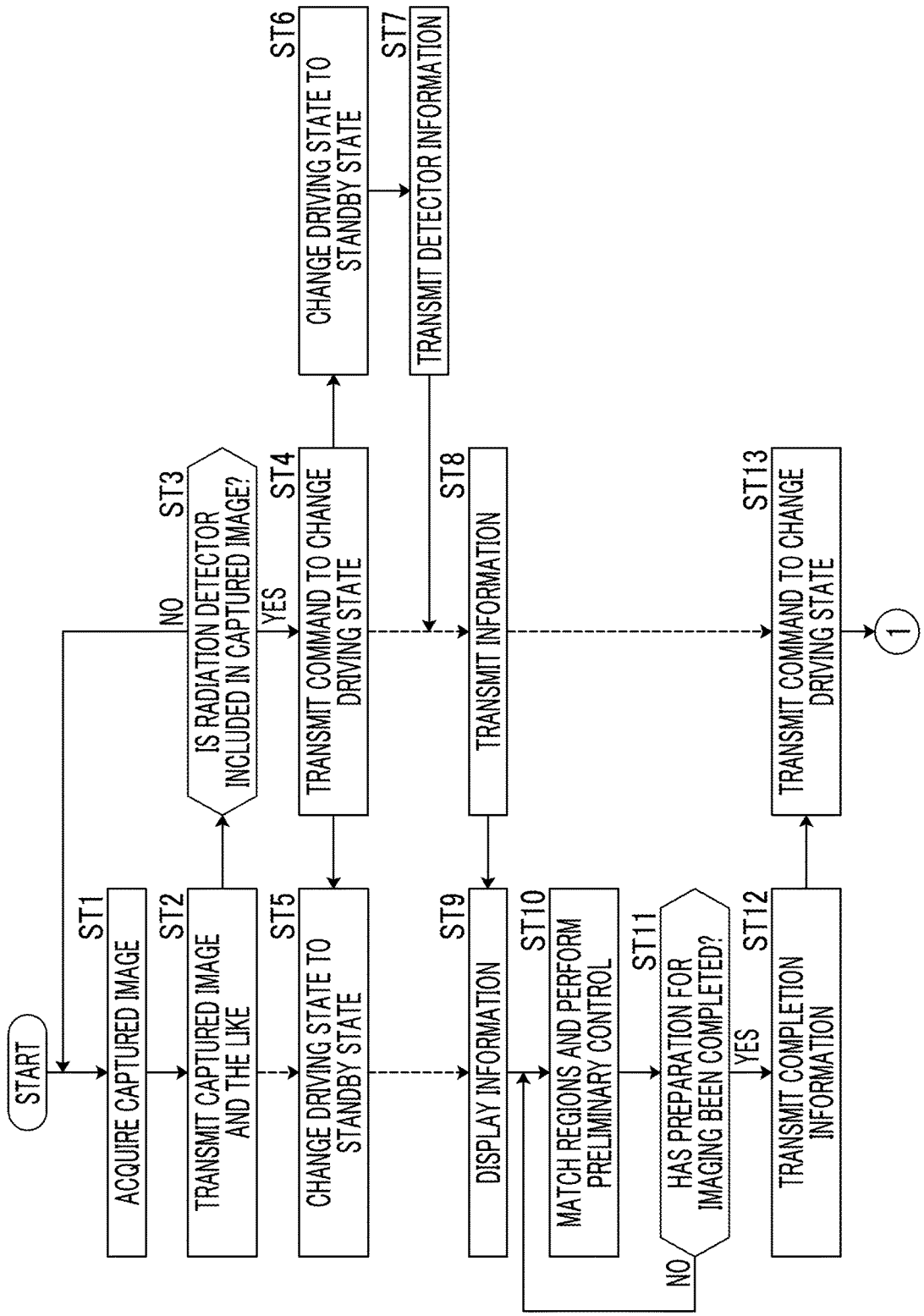
FIG. 10 is a flowchart illustrating a process performed in this embodiment.
Figure 11:
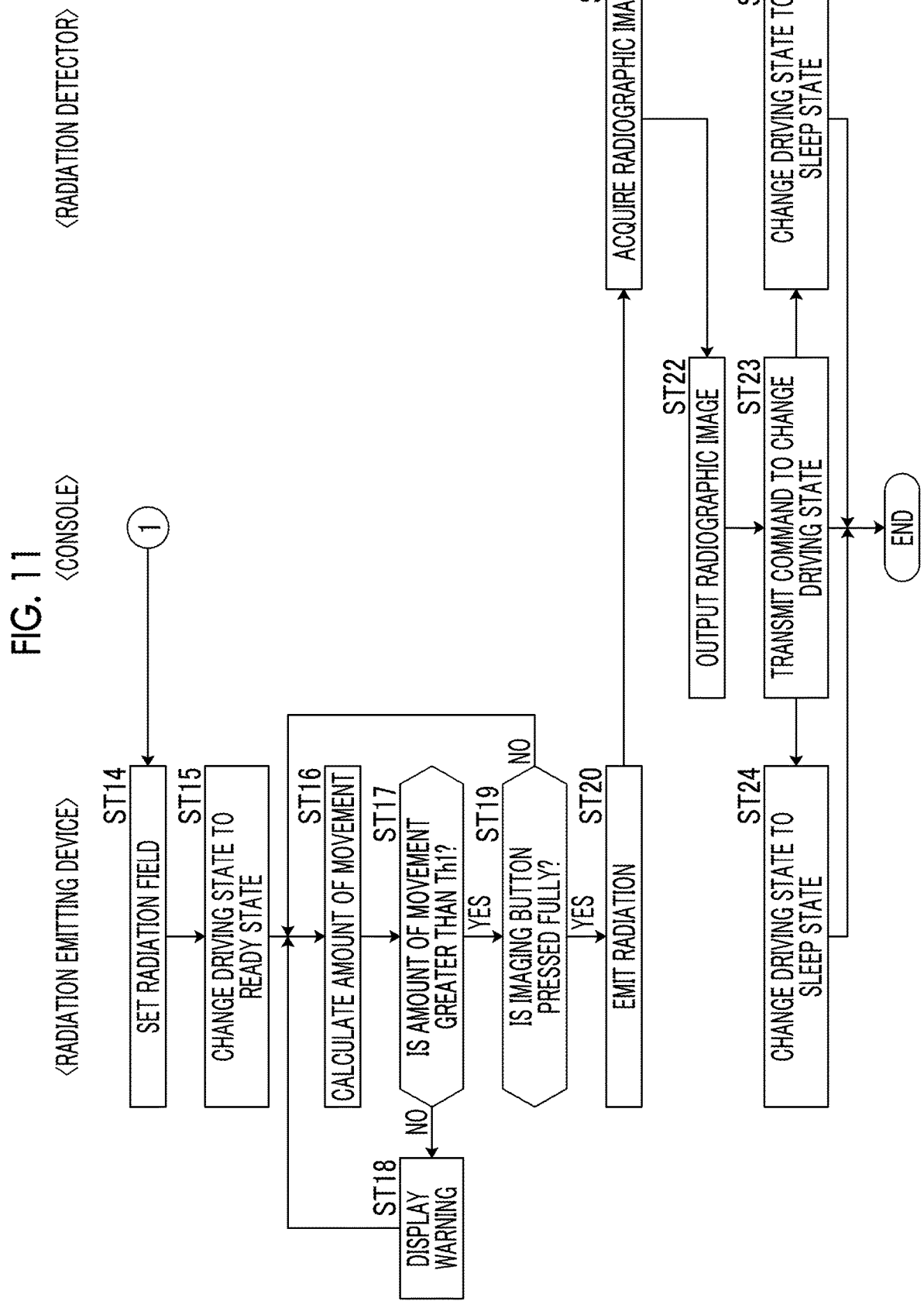
FIG. 11 is a flowchart illustrating a process performed in this embodiment.

Next, a process performed in this embodiment will be described below. FIGS. 10 and 11 are flowcharts illustrating the process performed in this embodiment. It is assumed that the radiation emitting device 10 and the radiation detector 30 are turned on and are in the sleep state. In addition, in the radiography apparatus according to this embodiment, it is assumed that two operators handle radiation emitting device 10 and the radiation detector 30 to perform a pre-imaging operation for setting the radiation detector 30 behind the subject H or setting the radiation field and perform an imaging operation after the pre-imaging operation is completed. Information indicating the movement of the radiation detector 30 detected by the motion sensor 38 is transmitted from the radiation detector 30 in the sleep state to the console 50. Furthermore, it is assumed that the distance sensor 27 detects the SID and the SOD before imaging. First, the radiation emitting device 10 is placed above the subject H, the camera 13 captures an image of the subject H, and the captured image G1 of the subject H is acquired (Step ST1).

The radiation emitting device 10 transmits the captured image G1, the SID, the SOD, and the information of the radiation field defined by the collimator 14 to the console 50 (the transmission of, for example, the captured image: Step ST2). The driving state control unit 53 of the console 50 determines whether the captured image G1 includes the radiation detector 30 (Step ST3). In a case in which the captured image G1 does not include the radiation detector 30 as illustrated in FIG. 8, the determination result in Step ST3 is "NO" and the process returns to Step ST1. In a case in which the captured image G1 includes the radiation detector 30 as illustrated in FIG. 9, the determination result in Step ST3 is "YES" and the driving state control unit 53 transmits a command to change the driving state from the communication unit 57 to the radiation emitting device 10 and the radiation detector 30 (Step ST4).

In the radiation emitting device 10, the driving control unit 23 changes the driving state of the radiation emitting device 10 to the standby state on the basis of the command to change the driving state (Step ST5). In addition, in the radiation detector 30, the driving control unit 36 changes the driving state of the radiation detector 30 to the standby state on the basis of the command to change the driving state (Step ST6).

In the radiation detector 30, the driving control unit 36 transmits detector information including information indicating the driving state of the radiation detector 30 and remaining battery level information indicating the remaining level of the battery 39 from the communication unit 37 to the console 50 (Step ST7). The communication unit 57 of the console 50 receives the detector information. The control unit 59 acquires information related to the detector which includes the identification information of the radiation detector 30, radiation detector position information indicating the position of the radiation detector 30 on the captured image G1, information indicating the vertical direction of the radiation detector 30, and the center position information of the radiation detector 30, on the basis of any one of the markers 34A to 34D of the radiation detector 30 included in the captured image G1. In addition, the control unit 59 subtracts the SOD from the SID to calculate the body thickness of the subject H and sets imaging conditions from the body thickness.

Figure 12:
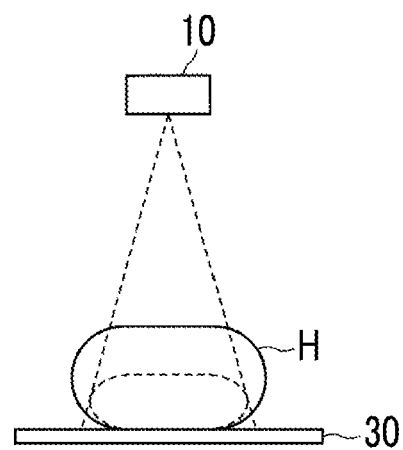
FIG. 12 is a diagram illustrating a change in a radiation field corresponding to the body thickness of the subject.

Here, the size of the field of the radiation emitted from the radiation emitting device 10 is different in a case in which the body thickness of the subject H is large and in a case in which the body thickness of the subject H is small, as illustrated in FIG. 12. Specifically, as the body thickness increases, the radiation field increases. Therefore, the control unit 59 calculates the body thickness of the subject H from the SID and the SOD and acquires information related to the radiation field which includes information about the size and the position of the center of a radiation field region, on the basis of the information of the range defined by the collimator 14 which has been transmitted from the radiation emitting device 10. Then, the control unit 59 transmits the detector information, the information related to the detector, the information related to the radiation field, and the imaging conditions to the radiation emitting device 10 (the transmission of information: Step ST8).

In addition, the imaging conditions may be set according to a part of the subject H included in the captured image G1. Information about the part of the subject H may be input to the radiation emitting device 10 by the operator and acquired. Alternatively, the information may be input through the input unit 56 of the console 50. In addition, an appropriate quality of radiation (whether the voltage is high or low) varies depending on the type of scintillator used in the image detection unit 31 provided in the radiation detector 30. Therefore, the imaging conditions may be set according to the material forming the scintillator used in the image detection unit 31 provided in the radiation detector 30, in addition to the body thickness. In this case, the storage unit 55 may store a table in which the information of the scintillator used in the image detection unit 31 and the imaging conditions, which correspond to the identification information of the radiation detector 30, are associated with each other. In this case, it is possible to set the imaging conditions corresponding to the identification information of the radiation detector 30 acquired from the captured image G1 with reference to the table. In addition, in a case in which imaging information obtained when an image of the same subject H is captured using the same radiation emitting device 10 and the same radiation detector 30 has been stored, the imaging conditions may be set, considering the imaging information.

Here, in a case in which the radiation detector 30 is moved after the radiation detector 30 is included in the captured image G1, the radiation detector 30 is moved to a position out of the angle of view of the camera 13 and the radiation detector 30 may not be included in the captured image G1. In addition, in a case in which the radiation detector 30 is completely hidden by the subject H, the radiation detector is not included in the captured image G1. In this case, since the markers 34A to 34D are not included in the captured image G1, it is difficult to specify, for example, the position of the radiation detector 30 from only the captured image G1.

Therefore, in this embodiment, in a case in which the radiation detector 30 is not included in the captured image G1, the control unit 59 acquires the movement information of the radiation detector 30 detected by the motion sensor 38. Then, the control unit 59 calculates the amount of movement of the radiation detector 30 from a reference position which is the position of any one of the markers 34A to 34D of the radiation detector 30 in a case in which any one of the markers 34A to 34D of the radiation detector 30 is included in the captured image G1, on the basis of the movement information and the size of the detection region of the radiation detector 30. Then, the control unit 59 acquires radiation detector position information on the basis of the calculated amount of movement. In this way, even in a case in which the radiation detector 30 is not included in the captured image G1, it is possible to track the position of the radiation detector 30.

The driving control unit 23 of the radiation emitting device 10 displays the identification information of the radiation detector 30, the driving state of the radiation detector 30, the vertical direction of the radiation detector 30, the remaining battery level of the radiation detector 30, the region corresponding to the radiation detector 30, the position of the center of the radiation detector 30, and the radiation field defined by the collimator 14 on the captured image G1 displayed on the monitor 15 so as to be superimposed thereon, on the basis of the information transmitted from the console 50 (display of information: Step ST9).

Figure 13:
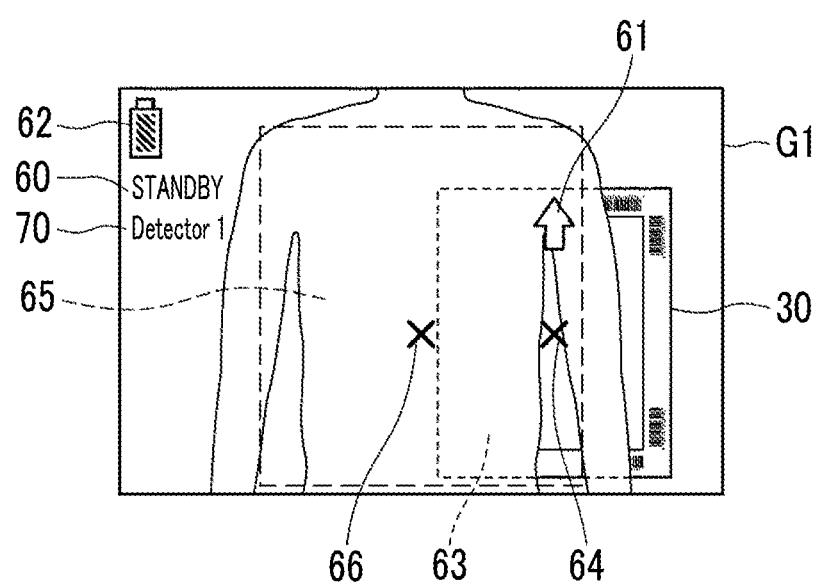
FIG. 13 is a diagram illustrating a captured image on which various kinds of information are superimposed.

FIG. 13 is a diagram illustrating the captured image G1 on which various kinds of information are superimposed. As illustrated in FIG. 13, a text (here, "standby") 60 indicating the driving state of the radiation detector 30, an arrow 61 indicating the vertical direction of the radiation detector 30, an icon 62 indicating the remaining battery level of the radiation detector 30, a detection region 63 corresponding to the detection region of the radiation detector 30, a center position 64 of the radiation detector 30, a radiation field region 65, a center position 66 of the radiation field region 65, and a text 70 "Detector1" which is the identification information of the radiation detector 30 are displayed on the captured image G1 displayed on the monitor 15 so as to be superimposed thereon. In addition, the center position 66 of the radiation field is displayed in the radiation field region 65. It is preferable that the detection region 63 and the radiation field region 65 are displayed so as to be distinguished from each other. For example, it is preferable that the color of the detection region 63 is different from the color of the radiation field region 65. The colors may be designated by a command from the console 50.

In the console 50, it is preferable that the control unit 59 detects the color of the clothes of the subject H from the captured image G1 and designates the colors of the detection region 63 and the radiation field region 65 so as to be different from the color of the clothes. In this case, it is possible to prevent the confusion between the color of the clothes of the subject H and the colors of the detection region 63 and the radiation field region 65 superimposed on the captured image G1.

Figure 14:
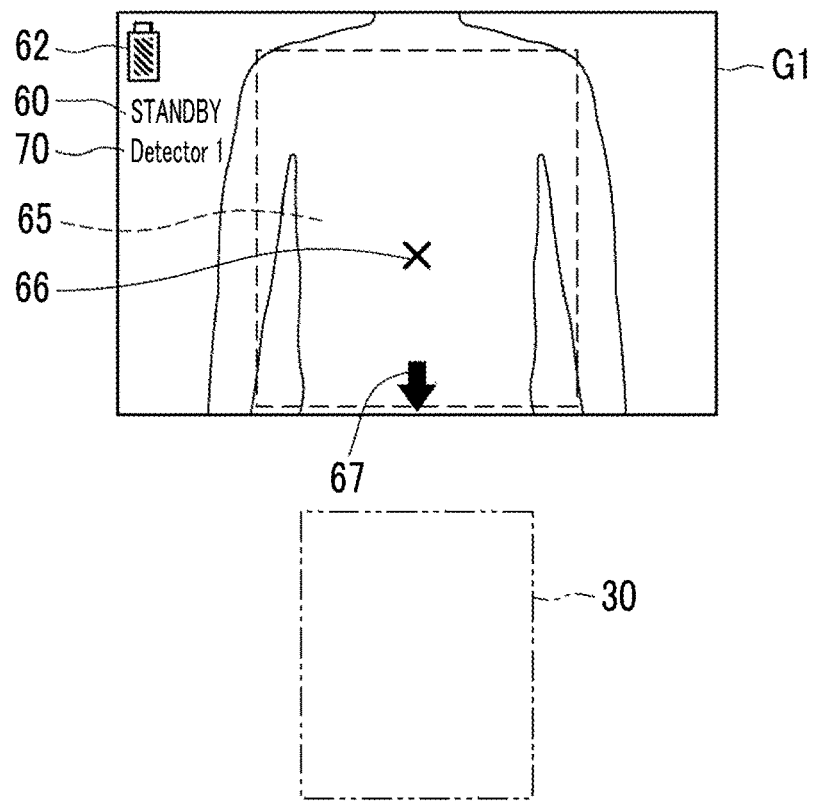
FIG. 14 is a diagram illustrating a captured image on which information a direction in which the radiation detector is present is superimposed.

In a case in which the radiation detector 30 is included in the captured image G1 and is then excluded from the captured image G1, information indicating the direction in which the radiation detector 30 is present in the captured image G1 may be displayed, using the radiation detector position information calculated on the basis of the movement information of the radiation detector 30. FIG. 14 is a diagram illustrating a captured image on which the information indicating the direction in which the radiation detector is present is superimposed, in addition to various kinds of information. In FIG. 14, the position of the radiation detector 30 is represented by a virtual line. As illustrated in FIG. 14, in addition to the information superimposed on the captured image G1 illustrated in FIG. 13, an arrow 67 indicating the direction in which the radiation detector 30 is present is displayed on the captured image G1 displayed on the monitor 15. Even in a case in which the radiation detector 30 is completely hidden behind the subject H, it is possible to specify the position of the radiation detector 30 in the captured image G1, using the radiation detector position information calculated on the basis of the movement information of the radiation detector 30. Therefore, it is possible to display the detection region 63 on the captured image G1.

Figure 15:
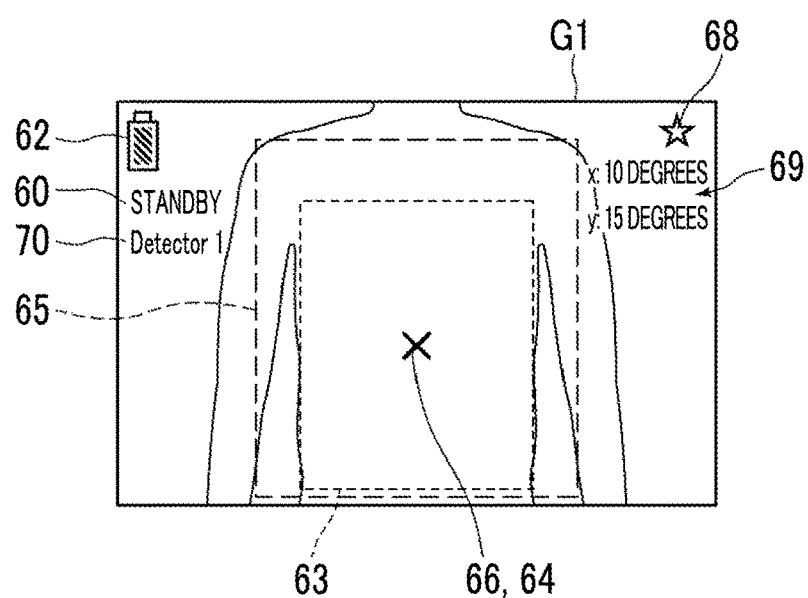
FIG. 15 is a diagram illustrating a state in which the center position of a radiation field region is matched with the center position of a detection region.

The operators of the radiation emitting device 10 and the radiation detector 30 perform a pre-imaging operation in cooperation with each other. That is, the operator of the radiation detector 30 moves the radiation detector 30 to an appropriate position behind the subject H and the operator of the radiation emitting device 10 checks whether the radiation detector 30 has been moved to an appropriate position while seeing the image displayed on the monitor 15. In addition, the operator moves the position of the radiation emitting device 10 if necessary. As illustrated in FIG. 15, the center position 66 of the radiation field region 65 and the center position 64 of the detection region 63 can be aligned with each other by this operation.

Furthermore, the control unit 59 may determine whether the center position of the radiation detector 30 has been aligned with the center position 66 of the radiation field region 65. In a case in which the positions have been aligned with each other, the control unit 59 may transmit information indicating the alignment to the radiation emitting device 10. In a case in which the information indicating the alignment is received, the radiation emitting device 10 displays information indicating that the center positions have been aligned with each other, such as a text "the center positions have been aligned with each other" or a mark indicating that the center positions have been aligned with each other, on the monitor 15. In FIG. 15, a star-shaped mark 68 indicates that the center positions have been aligned with each other. In addition, instead of displaying the text or the mark on the monitor 15, any method may be used as long as it can inform the operator that the center position of the radiation detector 30 has been aligned with the center position 66 of the radiation field region 65. For example, a method that outputs sounds or a method that blinks the monitor 15 may be used.

In a case in which the center position of the radiation detector 30 has been aligned with the center position 66 of the radiation field region 65, information about the tilt of the radiation detector 30 with respect to the radiation emitting device 10 may be displayed so as to be superimposed on the captured image G1, on the basis of the information about the tilt of the radiation detector 30 included in the movement information of the radiation detector 30. Here, the tilt of the radiation detector 30 with respect to the radiation emitting device 10 means a two-dimensional tilt with respect to the plane perpendicular to a radiation emission optical axis. In a case in which the x-axis and the y-axis are set on the plane of the radiation detector 30, the tilt is a tilt angle about each of the x-axis and the y-axis. In a case in which the center position of the radiation detector 30 has been aligned with the radiation emission axis, the control unit 59 of the console 50 acquires information about the tilt of the radiation detector 30 and transmits the information to the radiation emitting device 10. In a case in which the information about the tilt of the radiation detector 30 is received, the radiation emitting device 10 displays the angles about the x-axis and the y-axis on the monitor 15. FIG. 15 illustrates angle information 69 indicating the angles about the x-axis and the y-axis. In this way, the operator can adjust the tilt of the radiation detector 30 such that the angles of the radiation detector 30 about the x-axis and the y-axis are 0 and the radiation emission axis is perpendicular to the radiation detector 30.

In addition, the control unit 59 may calculate the relative tilt between the radiation emitting device 10 and the radiation detector 30, using the movement information of the radiation emitting device 10, and may transmit the calculated relative tilt to the radiation emitting device 10. In this case, after the radiation detector 30 is fixed, the tilt of the radiation emitting device 10 can be adjusted to adjust the relative tilt of the radiation detector 30 with respect to the radiation emitting device 10. In a case in which the radiation emission axis is perpendicular to the radiation detector 30, the color of the detection region 63 superimposed on the captured image G1 may be changed or the detection region 63 may be blinked. In this case, the operator can easily recognize that the radiation emission axis has been perpendicular to the radiation detector 30.

Here, in the state illustrated in FIG. 15, since the radiation field region 65 is larger than the detection region 63, it is difficult to convert a radiation component which has not been emitted to the radiation detector 30 among radiation components transmitted through the subject H into an image and the radiation component is unnecessary. In addition, the irradiation of the subject H with the unnecessary radiation component causes an increase in the amount of radiation emitted to the subject H.

Figure 16:
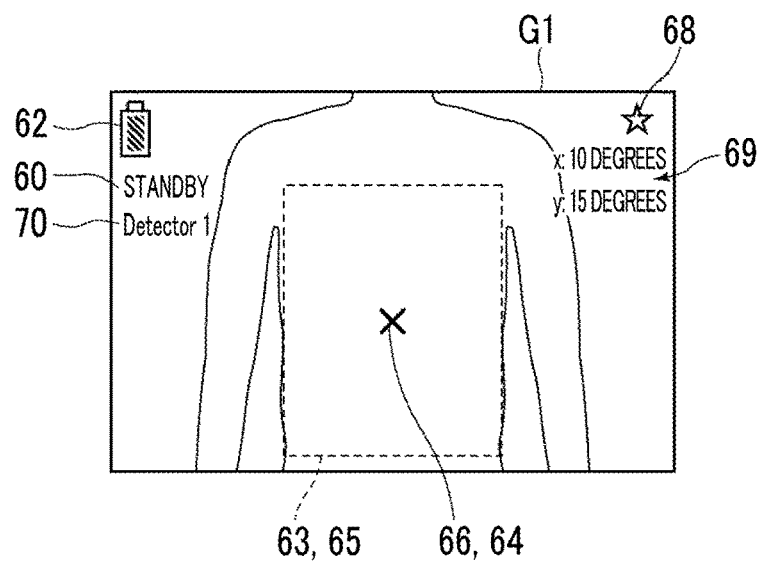
FIG. 16 is a diagram illustrating a state in which the radiation field region is matched with the detection region.

For this reason, the operator of the radiation emitting device 10 inputs a command to match the radiation field region 65 with the detection region 63, using the input unit 24. Then, the driving control unit 23 performs the following preliminary control in response to the command (the instruction of the matching between the regions and preliminary control: Step ST10). This command is a command that is input by the operation of, for example, the finger of the operator to match the radiation field region 65 displayed on the monitor 15 with the detection region 63, as illustrated in FIG. 16.

The collimator control unit 21 drives the collimator 14 in operative association with this command. In a case in which the collimator control unit 21 drives the collimator 14 whenever a command to match the radiation field region 65 with the detection region 63 is issued, power consumption increases. For this reason, in this embodiment, the collimator control unit 21 drives the collimator 14 in a case in which the issuing of the command to match the radiation field region 65 with the detection region 63 through the input unit 24 ends, preliminary control for driving the collimator 14 ends, and the input unit 24 receives input information indicating that preparation for imaging has been completed. The preliminary control is a control process of the driving control unit 23 predetermining how to set the radiation field region 65 on the basis of the captured image G1, that is, where the collimator 14 is driven to. The preliminary control will be described in detail below.

The driving control unit 23 of the radiation emitting device 10 determines whether the preparation for imaging has been completed (Step ST11). As described above, information indicating that the preparation for imaging has been completed may be received from the input unit 24. The imaging button 18 receives a two-stage operation. The imaging button 18 is pressed halfway to turn on the radiation field lamp 29 and is pressed fully to emit radiation. Therefore, the information indicating that the preparation for imaging has been completed may be received by an operation of pressing the imaging button 18 halfway. In this embodiment, it is assumed that the information indicating that the preparation for imaging has been completed is received by the operation of pressing the imaging button 18 halfway. In a case in which the determination result in Step ST11 is "NO", the process returns to Step ST10.

In a case in which the determination result in Step ST11 is "YES", the driving control unit 23 turns on the radiation field lamp 29 to transmit completion information indicating the preparation for imaging has been completed to the console 50 (Step ST12). In a case in which the driving state control unit 53 of the console 50 receives the completion information, the driving state control unit 53 transmits a command to change the driving state of the radiation emitting device 10 to the ready state to the radiation emitting device 10 (Step ST13). Then, the driving control unit 23 of the radiation emitting device 10 directs the collimator control unit 21 to drive the collimator 14 on the basis of the preliminary control, thereby setting the radiation field (Step ST14). At that time, it is preferable to notify the operator that the collimator 14 is being driven by, for example, blinking the radiation field region 65 displayed on the monitor 15.

In this case, since the radiation field lamp 29 is turned on, the subject H is irradiated with visible light through the collimator 14 driven to the position where the radiation field is set. Therefore, the operator can see the range of the visible light emitted to the subject H and check the radiation field region of the radiation emitted to the subject H from the range of the visible light in advance.

The driving control unit 23 of the radiation emitting device 10 does not receive the operation of the imaging button 18 while the collimator 14 is being driven. Then, in a case in which the driving of the collimator 14 is completed, the driving control unit 23 changes the driving state of the radiation emitting device 10 to the ready state (Step ST15).

In addition, the driving control unit 23 detects the movement of the radiation emitting device 10, using the motion sensor 28, and calculates the amount of movement of the radiation emitting device 10 per unit time (Step ST16). The amount of movement of the radiation emitting device 10 per unit time corresponds to the shaking of the hand of the operator. The driving control unit 23 determines whether the amount of movement per unit time is less than a threshold value Th1 (Step ST17). In a case in which the determination result in Step ST17 is "NO", the driving control unit 23 displays a warning on the monitor 15 (Step ST18) and returns to Step ST16. For example, the operator can take an action of firmly holding the radiation emitting device 10 in response to the displayed warning.

In a case in which the determination result in Step ST17 is "YES", the driving control unit 23 further determines whether the imaging button 18 has been pressed fully (Step ST19). In a case in which the determination result in Step ST19 is "NO", the driving control unit 23 returns to Step ST16. In a case in which the determination result in Step ST19 is "YES", the driving control unit 23 drives the radiation source 19 such that radiation is emitted to the subject H and the subject H is irradiated with the radiation (Step ST20). The radiation detector 30 detects the radiation transmitted through the subject H and acquires the radiographic image G2 of the subject H (Step ST21). The acquired radiographic image G2 is transmitted to the console 50 and the image processing unit 52 performs image processing for improving image quality and outputs the radiographic image G2 to the output unit 54 (Step ST22). The radiographic image G2 subjected to the image processing may be transmitted to the radiation emitting device 10 and the captured image G1 and the radiographic image G2 may be displayed on the monitor 15 so as to be superimposed on each other or only the radiographic image G2 may be displayed. In this way, it is possible to determine whether the radiographic image G2 has been appropriately acquired.

In a case in which the radiographic image G2 is acquired, the control unit 59 of the console 50 transmits a command to change the driving state of the radiation emitting device 10 and the radiation detector 30 to the sleep state to the radiation emitting device 10 and the radiation detector 30 (Step ST23). Then, each of the radiation emitting device 10 and the radiation detector 30 change the driving state to the sleep state (Steps ST24 and ST25) and the process ends.

As described above, in this embodiment, the collimator 14 is not driven in the stage in which the driving control unit 23 determines how to set the radiation field region 65, that is, where the collimator 14 is driven to, on the basis of the captured image G1. In a case in which the imaging button 18 is pressed halfway immediately before radiation is emitted, the collimator 14 is driven first. Therefore, it is possible to reduce the power consumption of the radiation emitting device 10 and to increase the life of the battery 26.

In this embodiment, the imaging button 18 is operated in two stages and also functions as an exposure switch for driving the radiation source and a light irradiation switch for driving the radiation field lamp 29. However, the invention is not limited thereto. The exposure switch and the light irradiation switch may be individually provided. In a case in which the light irradiation switch is pressed, the radiation field lamp 29 may be turned on and the driving control unit 23 may receive information indicating the completion of preparation for imaging. Then, in a case in which the exposure switch is pressed, the radiation source 19 may be driven.

As such, in a case in which the exposure switch and the light irradiation switch are individually provided, the collimator 14 may start to be driven when the light irradiation switch is pressed or the collimator 14 may start to be driven when the exposure switch is pressed. Similarly to the case in which the imaging button 18 is operated in two stages, the collimator 14 may start to be driven in a case in which the imaging button 18 is pressed halfway or the collimator 14 may start to be driven in a case in which the imaging button 18 is pressed fully. In a case in which the movement of the collimator 14 has been completed, the radiation source 19 may be driven.

In addition, for example, one joystick may be used to form the exposure switch and the light irradiation switch.

Figures 17A, 17B:
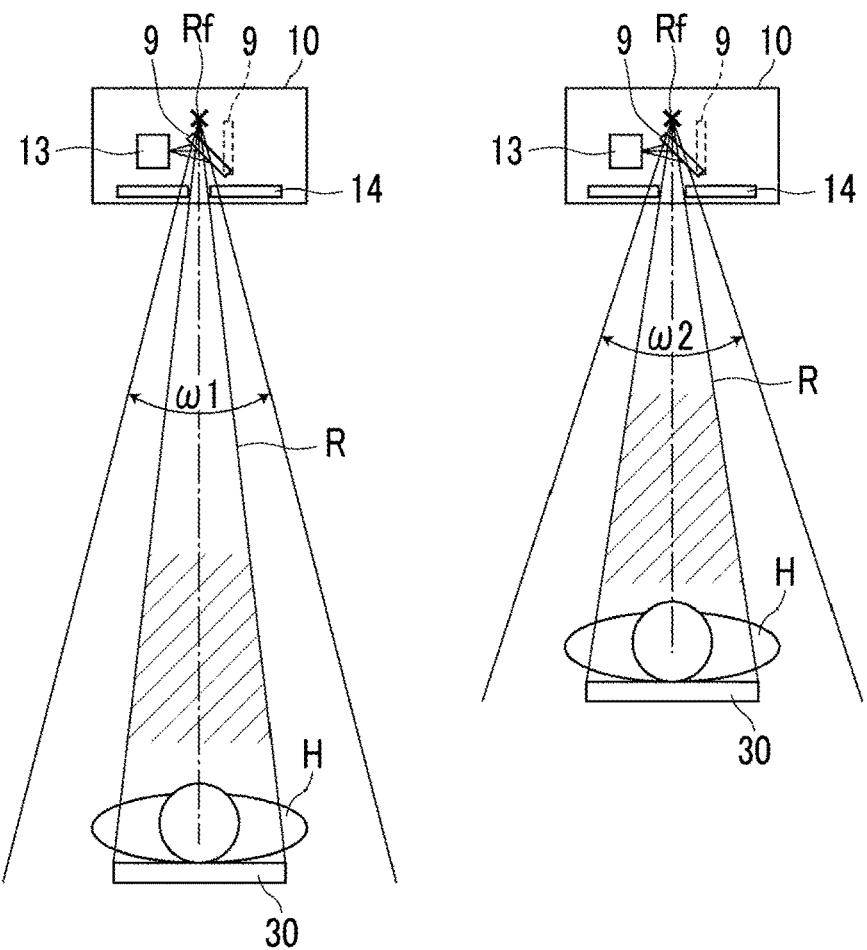
FIGS. 17A and 17B are diagrams schematically illustrating the method for determining the radiation field region.

Next, the preliminary control performed in Step ST10 of FIG. 10 will be described below. FIGS. 17A and 17B schematically illustrate the relationship between the angle of view of the camera 13 in the radiation emitting device 10 and the radiation field. In FIGS. 17A and 17B, 13 indicates a camera, 14 indicates a collimator, 30 indicates a radiation detector, 9 indicates a movable mirror that is inserted into a radiation emission path, R indicates radiation, and Rf indicates a radiation focus. The movable mirror 9 is set at a position that is represented by a solid line in FIGS. 17A and 17B in a case in which an optical image (captured image G1) of the subject H is captured by the camera 13 and is set at a position that is represented by a dashed line in FIGS. 17A and 17B in a case in which a radiographic image is captured. The camera 13 is provided at a position that is conjugate to the radiation focus through the movable mirror 9.

The same state as that in which the radiation field region 65 (which corresponds to the detection region 63 that is basically constant for each radiation detector 30) is present in the captured image G1 as illustrated in FIG. 16 occurs even in a case in which the subject H is relatively far away from the radiation emitting device 10 and is captured at a relatively small angle of view ω1 as illustrated in FIG. 17A or even in a case in which the subject H is relatively close to the radiation emitting device 10 and is captured at a relatively large angle of view ω2 as illustrated in FIG. 17B. As such, as the degree of opening of the collimator 14 is set to increase as the angle of view ω increases in order to make the radiation field region 65 of the radiation R present in the imaging range of the captured image G1 at a predetermined ratio.

For example, the driving control unit 23 illustrated in FIG. 4 calculates the degree of opening of the collimator 14 from the angle of view ω with reference to a look-up table in which the relationship between the angle of view ω and the degree of opening of the collimator 14 is stored. In addition, the driving control unit 23 calculates the angle of view ω from information related to the zoom magnification based on the operation of the zoom button 8 (see FIGS. 2 and 3). In a case in which a plurality of radiation detectors 30 are separately used, the look-up table may be prepared for the detection region 63 of each of the radiation detectors 30.

In the configuration illustrated in FIGS. 17A and 17B, it is preferable that the degree of opening of the collimator 14 is set to the minimum value in cases other than the case in which the captured image G1 is acquired. In this case, for example, it is possible to prevent the subject H from being carelessly irradiated with the radiation R.

The above-mentioned radiation field lamp 29 (see FIG. 4) can emit visible light along the emission path of the radiation R by, for example, the same mirror as the movable mirror 9 into the emission path of the radiation R so as to be withdrawn from the emission path. In this case, the collimator 14 is also used as a stop that narrows the emission range of visible light. However, the stop may be provided independently of the collimator 14, as shown by dotted line in FIG. 4.

Figure 18:
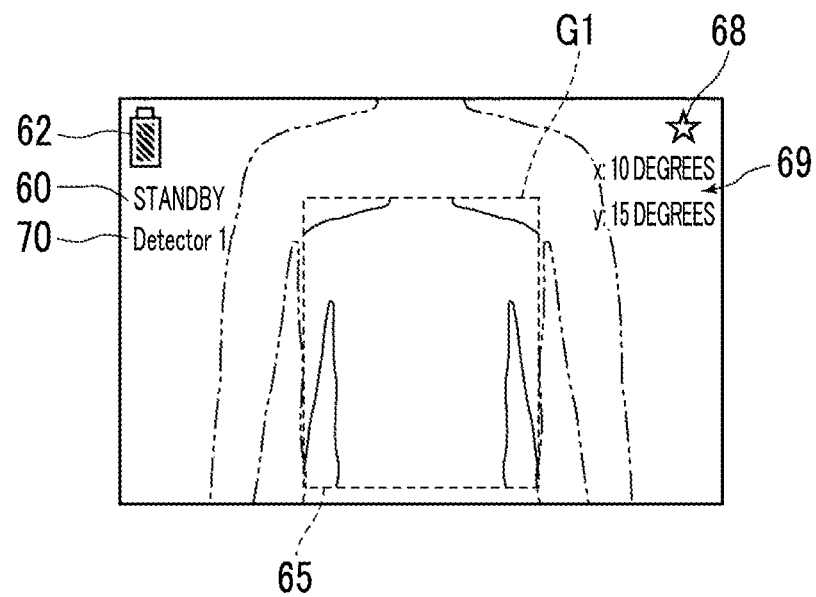
FIG. 18 is a diagram schematically illustrating the method for determining the radiation field region.

In the above-mentioned example, the radiation field region 65 is set in a partial range of the captured image G1. However, the entire captured image G1 may be set as the radiation field region 65. FIG. 18 illustrates an example of the display state of the monitor 15 in this case. In this case, the entire imaging range of the captured image G1 is displayed in a portion of the display range of the monitor 15. The operator sets the zoom magnification of the camera 13 such that the part of the subject H indicated by the captured image G1 is exactly in a desired radiation field region 65. For example, in a case in which an image of the subject H is captured as represented by a solid line in FIG. 18, the radiation field region 65 is a region from a lower part of the neck to the left and right upper extremities. In a case in which the zoom button 8 is operated to increase the zoom magnification such that the subject H is positioned with respect to the radiation field region 65 as represented by a two-dot chain line in FIG. 18, the radiation field region 65 is set in only the chest of the subject H.

Even in the above-mentioned case, for example, the degree of opening of the collimator 14 may be calculated from the zoom magnification with reference to the look-up table in which the relationship between the zoom magnification and the degree of opening of the collimator 14 is stored.

In the above-mentioned two examples, the radiation field region 65 set in a partial range of the captured image G1 is matched with the detection region 63 of the radiation detector 30. However, the radiation field region 65 may be set to other sizes. For example, the radiation field region 65 may be set to be smaller than the detection region 63 of the radiation detector 30 on the basis of a command input from the input unit 24 illustrated in FIG. 4. In this case, the input unit 24 corresponds to a partial range input unit according to the invention.

Figure 19:
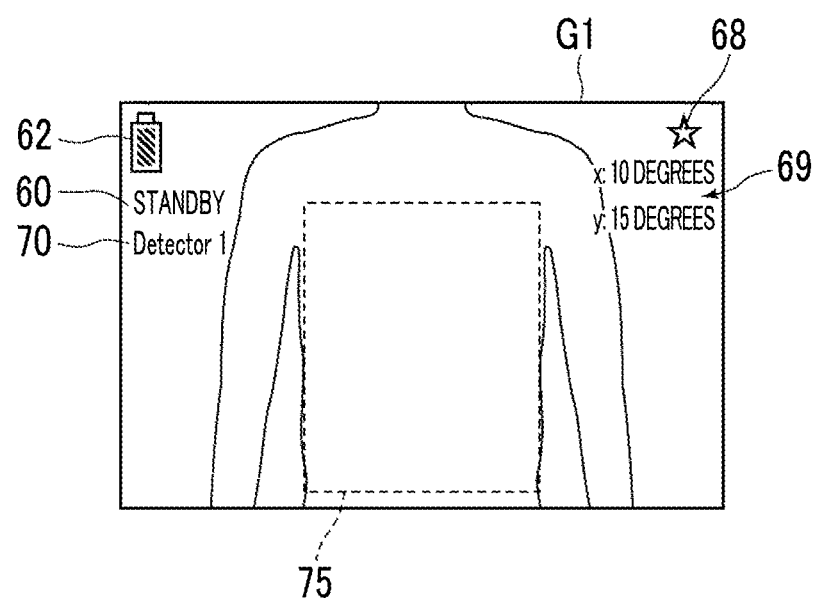
FIG. 19 is a diagram schematically illustrating the method for determining the radiation field region.

Next, another method for setting the radiation field region 65 will be described with reference to FIGS. 19 and 20. In this example, as illustrated in FIG. 19, the operator sets an arbitrary radiation field region in the captured image G1. This setting is performed by the input of information from the input unit 24 illustrated in FIG. 4. In particular, in this case, it is preferable that the monitor 15 which is a so-called touch panel is used as the input unit 24 and information is input from the monitor 15 by a touch operation such as a so-called "pinch" operation.

For example, as illustrated in FIG. 19, the arbitrary radiation field region is input as a rectangular region and is displayed as a rectangular frame together with the captured image G1 on the monitor 15. Hereinafter, this region is referred to as a set radiation field region 75. Instead of displaying the radiation field region as the frame, for example, a color, brightness, or contrast may be different inside and outside the radiation field region in the captured image G1 such that the radiation field region can be visibly recognized. In addition, in a case in which the radiation field region is displayed as the frame, the radiation field region is not necessarily displayed so as to be superimposed on the captured image G1. The radiation field region may be displayed side by side with the captured image G1 in the display region of the monitor 15.

In this case, the captured image G1 is an image captured by the camera 13 that uses a lens with a constant focal length and does not have a zoom function.

Figure 20:
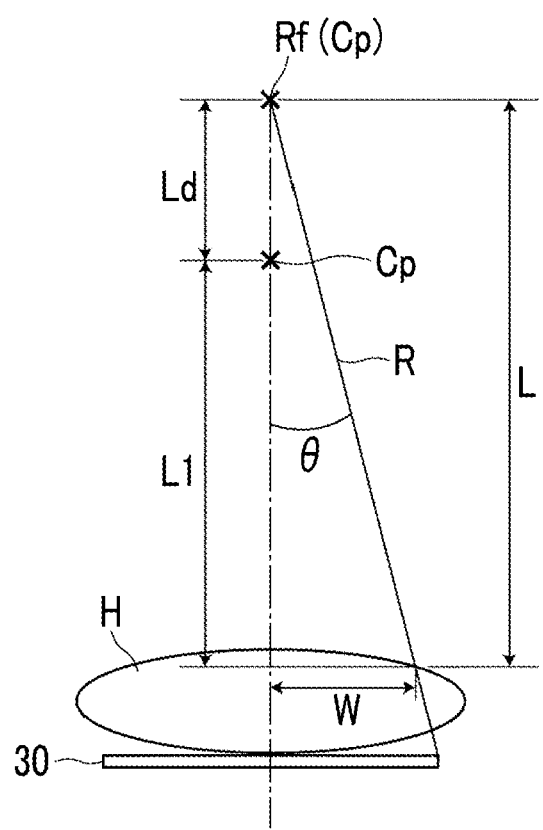
FIG. 20 is a diagram schematically illustrating the method for determining the radiation field region.

As illustrated in FIG. 20, in a case in which a region that is half of the set radiation field region 75 has a length W is considered and the distance from the subject H to the radiation focus Rf is L, the degree of opening of the collimator 14 may be set such that the radiation R is emitted at an angle θ from the radiation focus Rf. This holds for a direction perpendicular to the direction of the length W. The driving control unit 23 illustrated in FIG. 4 calculates the degree of opening of the collimator 14 from the angle θ, using the distance L that is automatically measured by the distance sensor 27 as distance measurement unit, as described above. In this case, the driving control unit 23 and the distance measurement unit form distance setting unit.

The case in which the position of the camera 13 which is represented by (Cp) in FIG. 20 is conjugate to the radiation focus Rf has been described above. In a case in which the position of the camera 13 is separated from the radiation focus Rf as represented by Cp in FIG. 20, a known distance Ld between the camera 13 and the radiation focus Rf may be added to a distance L1 from the subject H to the camera 13 which is automatically measured by the distance sensor 27 disposed at a position that is substantially the same as the position of the camera 13 and the angle θ may be calculated from the sum of the distance Ld and the distance L1 and the length W.

In this case, the distance L or L1 automatically measured by the distance sensor 27 is used. However, the operator may actually measure the distances and input the measured distances through the input unit 24 illustrated in FIG. 4.

The radiation emitting device 10 according to this embodiment is portable and can emit radiation to the direction in which the subject H is absent. In order to prevent this situation, it is preferable that the driving control unit 23 controls the radiation source 19 such that radiation is not capable of being emitted in a state in which an object required for imaging, such as the radiation detector 30, is not included in the captured image G1.

In the above-described embodiment, the control unit 59 of the console 50 sets imaging conditions. However, the control unit 59 may determine whether radiation can be emitted according to the set imaging conditions, on the basis of information about the remaining level of the battery 26 in the radiation emitting device 10. In a case in which radiation is not capable of being emitted according to the set imaging conditions, information indicating that radiation is not capable of being emitted may be transmitted to the radiation emitting device 10. The radiation emitting device 10 can display information indicating that imaging is not available on the monitor 15 such that the operator can recognize that the remaining level of the battery 26 is insufficient. Therefore, the operator can take, for example, an action of replacing the battery 26 or an action of preparing another radiation emitting device 10.

In the above-described embodiment, in some cases, the amount of movement of the radiation emitting device 10 per unit time is equal to or greater than the threshold value Th1 while radiation is being emitted. In this case, the emission of radiation may be temporarily stopped and radiation may be emitted for the remaining radiation emission time in a case in which the amount of movement of the radiation emitting device 10 per unit time is less than the threshold value Th1. In this case, two radiographic images are acquired before and after the emission of radiation is stopped. The console 50 may combine the two radiographic images using, for example, an addition process to generate a final radiographic image G2.

In the above-described embodiment, the driving state of both the radiation emitting device 10 and the radiation detector 30 is controlled on the basis of whether the radiation detector 30 is included in the captured image G1. However, the driving state of only the radiation emitting device 10 may be controlled or the driving state of only the radiation detector 30 may be controlled.

In the above-described embodiment, the console 50 may transmit the generated radiographic image G2 to the radiation emitting device 10. In this case, the radiation emitting device 10 can display the radiographic image G2 on the monitor 15 such that the operator checks whether imaging has succeeded. In this case, the captured image G1 and the radiographic image G2 may be displayed side by side or may be displayed such that the radiographic image G2 is superimposed on the captured image G1.

In the above-described embodiment, the imaging button 18 is pressed halfway to turn on the radiation field lamp 29. However, the turn-on and turn-off the radiation field lamp 29 may be switched. For example, in a case in which the radiographic image G2 of the face of an animal is acquired, it is necessary to irradiate the face of the animal with radiation. In this case, when the radiation field lamp 29 is turned on, light is emitted to the face of the animal is likely to become wild. For this reason, the control unit 59 of the console 50 may determine a part of the subject H included in the captured image G1. In a case in which the part is the face of the animal, control unit 59 may not turn on the radiation field lamp 29 even when the imaging button 18 is pressed halfway. In this case, it is possible to prevent animals from becoming wild due to visible light emitted from the radiation field lamp 29. Since the operator knows the part of the subject H, the turn-on and turn-off of the radiation field lamp 29 may be switched by a command input by the operator through the input unit 24.

In the above-described embodiment, the camera 13 may be an infrared camera that can measure a temperature distribution in an imaging range using infrared rays and an infrared image indicating the temperature distribution in the imaging range may be used as the captured image G1. In this case, the captured image G1 acquired by the camera 13 indicates the temperature distribution of the surface of the subject H and the surface of an object in the vicinity of the subject H. The use of the camera 13 that can acquire an infrared image as the captured image G1 makes it possible to specify the position of the subject H on the captured image G1 on the basis of the temperature distribution indicated by the captured image G1 even in a case in which the subject H is covered with, for example, a sheet in a disaster site.

It is preferable that the camera 13 is switched between an imaging mode using visible light and an imaging mode using infrared rays. In a case in which the camera 13 that is switched between the imaging mode using visible light and the imaging mode using infrared rays is used, first, an image of the subject H is captured using infrared rays and the captured image G1 indicating a temperature distribution is acquired. Then, the position of the radiation field is determined using the captured image G1 indicating the temperature distribution. Then, the camera 13 may be switched to the imaging mode using visible light. Then, as in the above-described embodiment, the detector region of the radiation detector 30 and the radiation field region may be displayed so as to be superimposed on the captured image G1. Then, the position of the radiation detector 30 may be determined using the captured image G1 such that the detection region of the radiation detector 30 and the radiation field region are matched with each other. In this case, even in a case in which the subject H is covered with, for example, a sheet, it is possible to match the radiation field region with the detection region of the radiation detector 30 and to acquire the radiographic image G2.

As such, the captured image G1 which is an infrared image is displayed on the monitor 15 such that the operator can recognize abnormality in the body temperature of the subject H. In addition, the captured radiographic image G2 and the captured image G1 which is an infrared image may be displayed side by side on the monitor 15. In this case, the infrared image can be compared with the radiographic image G2.

Figure 21:
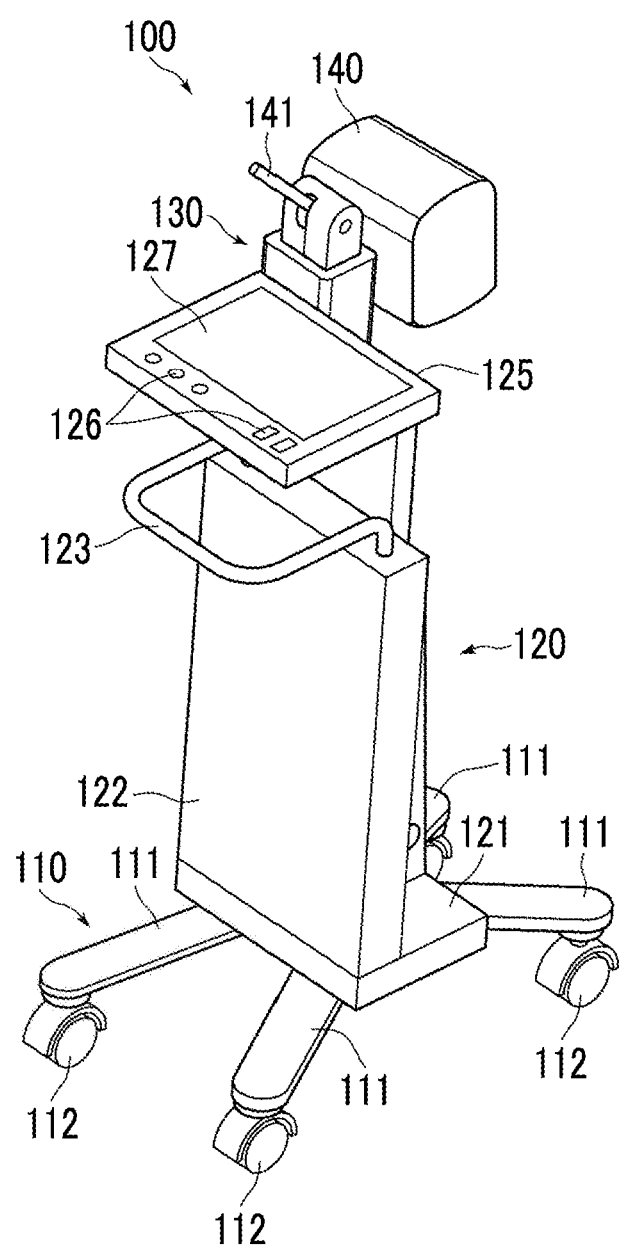
FIG. 21 is a perspective view illustrating the overall shape of a radiation emitting device according to another embodiment of the invention.
Figure 22:
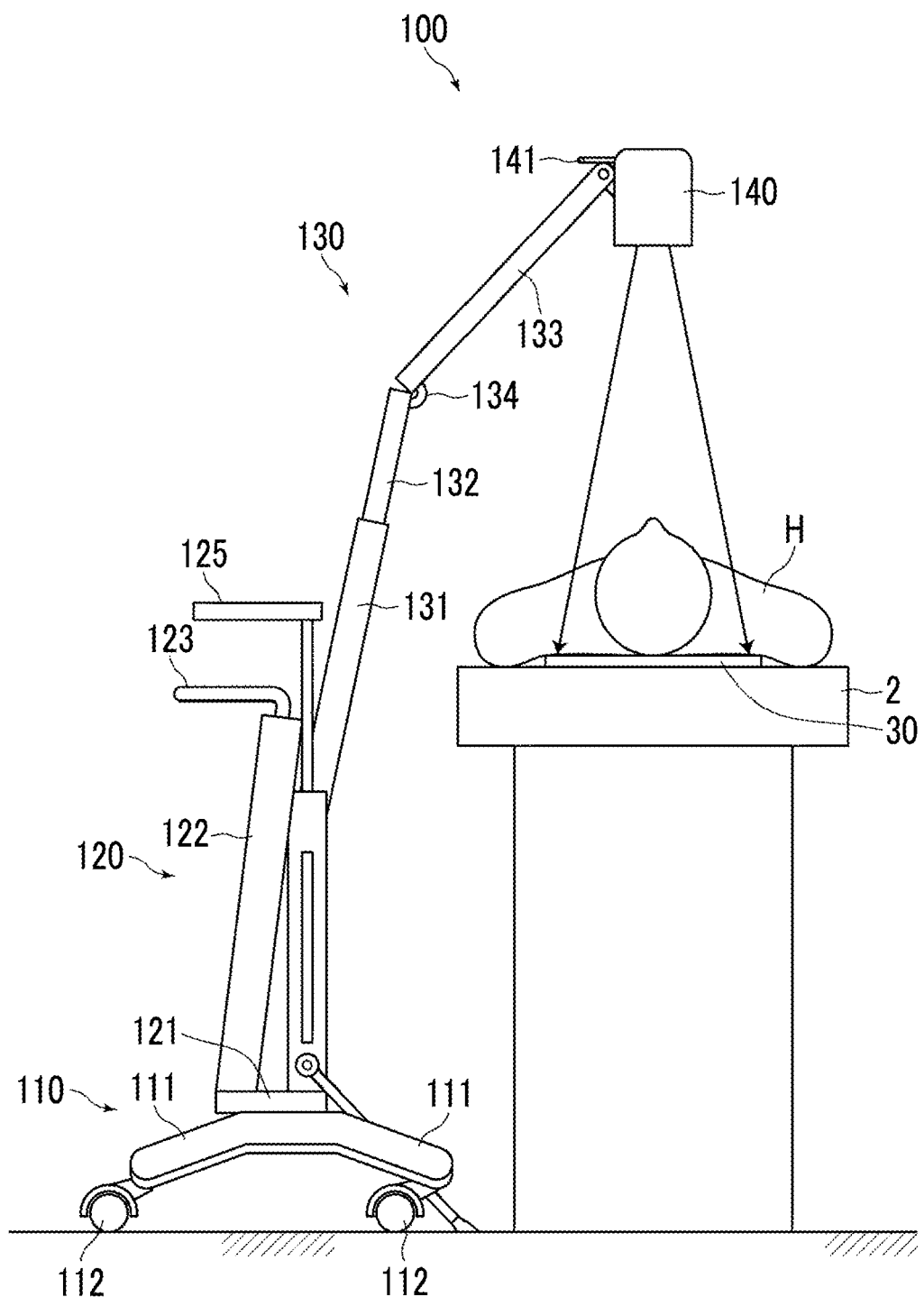
FIG. 22 is a side view illustrating the usage state of the radiation emitting device illustrated in FIG. 21.

In the above-described embodiment, the portable radiation emitting device 10 is used. However, a movable radiation emitting device may be used. FIG. 21 is a perspective view illustrating the overall shape of a movable radiation emitting device and FIG. 22 is a diagram illustrating the usage state of the radiation emitting device illustrated in FIG. 21. A radiation emitting device 100 illustrated in FIGS. 21 and 22 includes a leg portion 110 that can be moved on a device mounting surface, a main body portion 120 that is held on the leg portion 110, an arm portion 130 that is connected to the main body portion 120, and a radiation source unit 140 that is attached to a leading end of the arm portion 130.

The leg portion 110 includes four legs 111 and wheel portions 112 that are attached to a lower surface of a leading end of each leg 111. The wheel portion 112 is provided with brake means (not illustrated).

In the main body portion 120, an irradiation control unit 20, a collimator control unit 21, an imaging control unit 22, a driving control unit 23, a communication unit 25, and a battery 26 which are the same as those in the radiation emitting device 10 according to the above-described embodiment are accommodated in a housing 122 that is fixed to an upper part of the base portion 121. A handle 123 for moving the radiation emitting device 100 is attached to an upper end of the housing 122. In addition, an operation unit 125 is attached to the upper part of the base portion 121.

The operation unit 125 includes, for example, an input unit 126 including operation buttons or switches for inputting signals for instructing various operations of the radiation emitting device 100 and a monitor 127 for displaying various kinds of information. In addition, the input unit 126 may be a touch panel as in the radiation emitting device 10 according to the above-described embodiment.

The arm portion 130 includes a plurality of members 131, 132, and 133 having a nesting structure. The member 132 and the member 133 are connected to each other by a rotation holding mechanism 134. The member 133 is rotated with respect to the member 132 in a direction in which the angle is changed.

The radiation source unit 140 is pivotably attached to the leading end of the member 133 of the arm portion 130. The radiation source unit 140 is provided with a camera 13, a collimator 14, a radiation source 19, a distance sensor 27, a motion sensor 28, and a radiation field lamp 29 that are the same as those in the radiation emitting device 10 according to the above-described embodiment. A locking lever 141 can be operated to fix the pivot position of the pivotable radiation source unit 140.

In the radiation emitting device 100, the captured image G1 of the subject acquired by the camera 13 is displayed on the monitor 127 of the operation unit 125.

In a case in which a pre-imaging operation is performed, the operator extends the arm portion 130 and sets the length of the arm portion 130 and the pivot position of the radiation source unit 140 on the upper side of the subject H such that the radiation source unit 140 is located immediately above the subject H. In this state, the camera 13 captures an image of the subject H. In a case in which the radiation field region determined from the captured image G1 is set, a collimator driving command is controlled by the same method as that in the above-described embodiment. According to this structure, it is possible to reduce power consumption.

In a case in which the radiation emitting device 100 is used and the driving state of the device 100 is changed to the ready state, it is preferable that brake means (not illustrated) is driven to prevent the rotation of the wheel portions 112. In this case, it is possible to prevent the unexpected movement of the radiation emitting device 100 during imaging. Therefore, it is possible to prevent the blur of an acquired radiographic image.

In the present disclosure, the "captured image of the imaging target" is an image related to the imaging target in an imaging range of the imaging unit. The imaging target may include, for example, a subject, such as a person, or may not include the subject. The captured image of the imaging target also includes an infrared image which is acquired by capturing an image of the imaging target using infrared rays and indicates the temperature distribution of the surface of the imaging target and the surface of objects in the vicinity of the imaging target.

The "collimator" and the "stop" may be the same unit or may be individually provided.

In a case in which a switch has a certain degree of operation stroke and is turned on after the stroke, the "operation" includes the stroke.

In the present disclosure, "the radiation emitting device according to the invention" indicates both the first radiation emitting device and the second radiation emitting device.

In the radiation emitting device according to the invention, preferably, the imaging unit is imaging unit with a zoom function, and the control unit sets a part of an imaging range of the captured image which has been captured by the imaging unit and displayed on the display unit as the radiation field region.

Here, preferably, the partial range is determined so as to correspond to a detection region of a radiation detector that detects the radiation transmitted through the imaging target.

Alternatively, the radiation emitting device may further comprise a partial range input unit that sets the partial range. The partial range may be determined by an input from the partial range input unit.

In the radiation emitting device according to the invention, the imaging unit may be imaging unit with a zoom function and the control unit may set an imaging range of the captured image which has been captured by the imaging unit and displayed on the display unit as the radiation field region.

In the radiation emitting device according to the invention further comprise an input unit that displays information indicating the radiation field region together with the captured image displayed on the display unit. The control unit may set the radiation field region on the basis of the information indicating the radiation field region.

In the case of the above-mentioned configuration, preferably, the information indicating the radiation field region is a frame corresponding to the radiation field region. In particular, it is preferable that the frame is displayed so as to be superimposed on the captured image.

Preferably, in a case in which the radiation emitting device according to the invention further comprises an input unit that displays information indicating the radiation field region and the control unit sets the radiation field region on the basis of the information indicating the radiation field region, the radiation emitting device further comprises distance setting unit for setting a distance between the radiation source and the imaging target. Preferably, the control unit sets the radiation field region on the basis of the radiation field region indicated by the information and the distance set by the distance setting unit.

Preferably, the distance setting unit comprises distance measurement unit and sets the distance on the basis of a distance measured by the distance measurement unit.

The distance setting unit may set the distance on the basis of input distance information.

In the radiation emitting device according to the invention, preferably, in a case in which the light irradiation switch is operated after the control unit sets the radiation field region, the imaging unit captures the image of the imaging target.

In the radiation emitting device according to the invention, preferably, a battery is used as a driving source.

In the radiation emitting device according to the invention, preferably, the imaging unit acquires, as the captured image, an infrared image indicating a temperature distribution in the imaging range, using infrared rays. Preferably, the display unit displays the captured image which is the infrared image and a radiographic image of the imaging target.

According to the invention, the collimator driving command to direct the collimator to set the radiation field region determined from the captured image displayed by the display unit is issued to the collimator in a case in which the light irradiation switch or the exposure switch is operated. Therefore, the collimator is not sequentially driven until the light irradiation switch or the exposure switch is operated, which results in a reduction in power consumption.

What is claimed is:

1. An x-ray radiation emitting device comprising:
   an x-ray radiation source that emits x-ray radiation to an imaging target;
   a collimator that sets an x-ray radiation field region;
   a visible light source that emits visible light;
   a camera for capturing an image of the imaging target;
   a display unit that displays the image captured by the camera;
   a single button that drives the x-ray radiation source in a first operation mode and drives the visible light source in a second operation mode; and
   a control unit that issues a collimator driving command to direct the collimator to set the x-ray radiation field region determined from the captured image displayed by the display unit to the collimator in a case in which the single button is operated under either the first operation mode or the second operation mode.

2. The x-ray radiation emitting device according to claim 1,
   wherein the camera includes a zoom function, and
   the control unit sets a part of an imaging range of the captured image which has been captured by the camera and displayed on the display unit as the x-ray radiation field region.

3. The x-ray radiation emitting device according to claim 2,
   wherein the part of the imaging range is determined so as to correspond to a detection region of an x-ray radiation detector that detects the x-ray radiation transmitted through the imaging target.

4. The x-ray radiation emitting device according to claim 2, further comprising:
   a partial range input unit that sets the partial range,
   wherein the partial range is determined by an input from the partial range input unit.

5. The x-ray radiation emitting device according to claim 1,
   wherein the camera includes a zoom function, and
   the control unit sets an imaging range of the captured image which has been captured by the camera and displayed on the display unit as the x-ray radiation field region.

6. The x-ray radiation emitting device according to claim 1, further comprising:
   an input unit that displays information indicating the x-ray radiation field region together with the captured image displayed on the display unit,
   wherein the control unit sets the x-ray radiation field region on the basis of the information indicating the x-ray radiation field region.

7. The x-ray radiation emitting device according to claim 6,
   wherein the information indicating the x-ray radiation field region is a frame corresponding to the x-ray radiation field region.

8. The x-ray radiation emitting device according to claim 6, further comprising:
   distance setting unit for setting a distance between the x-ray radiation source and the imaging target,
   wherein the control unit sets the x-ray radiation field region on the basis of the x-ray radiation field region indicated by the information and the distance set by the distance setting unit.

9. The x-ray radiation emitting device according to claim 8,
   wherein the distance setting unit comprises distance measurement unit and sets the distance on the basis of a distance measured by the distance measurement unit.

10. The x-ray radiation emitting device according to claim 8,
    wherein the distance setting unit sets the distance on the basis of input distance information.

11. The x-ray radiation emitting device according to claim 1,
    wherein a battery is used as a driving source.

12. The x-ray radiation emitting device according to claim 1,
    wherein the camera acquires, as the captured image, an infrared image indicating a temperature distribution in the imaging range, using infrared rays, and
    the display unit displays the captured image which is the infrared image and a radiographic image of the imaging target.

13. The x-ray radiation emitting device of claim 1, further comprising:
    a stop that is disposed separately from the collimator and that matches an irradiation range of the visible light on the imaging target with the x-ray radiation field region;
    and the single button also drives the visible light source;
    and
    wherein the control unit directs the collimator to set the x-ray radiation field region determined from the captured image displayed by the display unit to the collimator in a case in which the single button is operated to drive the visible light source.

14. The x-ray radiation emitting device according to claim 13,
    wherein, in a case in which the single button is operated after the control unit sets the x-ray radiation field region, the camera captures the image of the imaging target.

15. A method for controlling an x-ray radiation emitting device comprising an x-ray radiation source that emits x-ray radiation to an imaging target, a collimator that sets an x-ray radiation field region, a visible light source that emits visible light; camera for capturing an image of the imaging target, a display unit that displays the image captured by the camera, and a single switch that drives the x-ray radiation source in a first operation mode and drives the visible light source in a second operation mode, the method comprising:

issuing a collimator driving command to direct the collimator to set the x-ray radiation field region determined from the captured image displayed by the display unit to the collimator in a case in which the single switch is operated under either the first operation mode or the second operation mode.

16. A method for controlling an x-ray radiation emitting device comprising an x-ray radiation source that emits x-ray radiation to an imaging target, a collimator that sets an x-ray radiation field region, a visible light source that emits visible light, a stop that is disposed separately from the collimator and that matches an irradiation range of the visible light on the imaging target with the x-ray radiation field region, camera for capturing an image of the imaging target, a display unit that displays the image captured by the camera, and a single switch that drives the visible light source, the method comprising:

issuing a collimator driving command to direct the collimator to set the x-ray radiation field region determined from the captured image displayed by the display unit to the collimator in a case in which the single switch is operated.

17. A non-transitory computer-readable storage medium storing a program that causes a computer to perform a method for controlling an x-ray radiation emitting device comprising an x-ray radiation source that emits x-ray radiation to an imaging target, a collimator that sets an x-ray radiation field region, a visible light source that emits visible light; camera for capturing an image of the imaging target, a display unit that displays the image captured by the camera, and a single switch that drives the x-ray radiation source in a first operation mode and drives the visible light source in a second operation mode, the program comprising:

a procedure of issuing a collimator driving command to direct the collimator to set the x-ray radiation field region determined from the captured image displayed by the display unit to the collimator in a case in which the single switch is operated under either the first operation mode or the second operation mode.

18. A non-transitory computer-readable storage medium storing a program that causes a computer to perform a method for controlling an x-ray radiation emitting device comprising an x-ray radiation source that emits x-ray radiation to an imaging target, a collimator that sets an x-ray radiation field region, a visible light source that emits visible light, a stop that is disposed separately from the collimator and that matches an irradiation range of the visible light on the imaging target with the x-ray radiation field region, camera for capturing an image of the imaging target, a display unit that displays the image captured by the camera, and a single switch that drives the visible light source, the program comprising:

a procedure of issuing a collimator driving command to direct the collimator to set the x-ray radiation field region determined from the captured image displayed by the display unit to the collimator in a case in which the single switch is operated.

19. An x-ray radiation emitting device comprising:

an x-ray radiation source that emits x-ray radiation to an imaging target;

a collimator that sets an x-ray radiation field region;

a visible light source that emits visible light;

a camera for capturing an image of the imaging target;

a display unit that displays the image captured by the camera;

a memory storing a look-up table in which a relationship between a camera parameter and a degree of opening of the collimator is stored;

a button that drives the x-ray radiation source in a first operation mode when fully pressed and drives the visible light source in a second operation mode when pressed halfway; and a control unit that:

performs a preliminary control, in which the preliminary x-ray radiation region is set from the captured image displayed by the display unit using the camera parameter stored in the look-up table and in which the collimator is not operated; and performs a main control by issuing a collimator driving command to direct the collimator to set the actual x-ray radiation field region to match the preliminary x-ray radiation region when the button is pressed halfway or pressed fully.

* * * * *